(12) United States Patent
Torbert, III et al.

(10) Patent No.: US 10,458,930 B2
(45) Date of Patent: Oct. 29, 2019

(54) METHODS AND SYSTEMS FOR NON-INVASIVE MEASUREMENT OF SOIL CHLORINE AND/OR NITROGEN CONTENT AND FOR DETECTING SUB-SURFACE CHLORINE OR NITROGEN-CONTAINING OBJECTS

(71) Applicant: The United States of America, as represented by the Secretary of Agriculture, Washington, DC (US)

(72) Inventors: Henry A. Torbert, III, Auburn, CA (US); Stephen A. Prior, Auburn, AL (US); Aleksandr G. Kavetskiy, Auburn, AL (US); Galina N. Yakubova, Auburn, AL (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 37 days.

(21) Appl. No.: 15/495,565

(22) Filed: Apr. 24, 2017

(65) Prior Publication Data

US 2017/0307550 A1    Oct. 26, 2017

Related U.S. Application Data

(60) Provisional application No. 62/327,039, filed on Apr. 25, 2016.

(51) Int. Cl.
*G01N 23/22*   (2018.01)
*G01N 33/24*   (2006.01)
*G01V 5/00*    (2006.01)

(52) U.S. Cl.
CPC ............ *G01N 23/22* (2013.01); *G01N 33/24* (2013.01); *G01V 5/00* (2013.01); *G01N 2223/616* (2013.01); *G01N 2223/652* (2013.01)

(58) Field of Classification Search
None
See application file for complete search history.

(56) References Cited

U.S. PATENT DOCUMENTS

| | | | | |
|---|---|---|---|---|
| 4,152,590 A | * | 5/1979 | Smith, Jr. | G01V 5/105 250/264 |
| 5,410,575 A | * | 4/1995 | Uhm | G01V 5/0008 376/159 |
| 2012/0199746 A1 | * | 8/2012 | Nose | G01N 23/222 250/358.1 |

* cited by examiner

*Primary Examiner* — Edwin C Gunberg
(74) *Attorney, Agent, or Firm* — John D. Fado; Robert D. Jones

(57) ABSTRACT

The presence of chlorine and nitrogen are determined and measured using a non-invasive portable neutron-generating and gamma ray detecting system(s). Portable devices of the present invention can also be used to detect chlorine and/or nitrogen-containing underground objects rapidly and on-site. Devices and systems described herein can be operated remotely and pre-programmed with search patterns, guided by an operator remotely, or programmed to home in on high-chlorine and/or nitrogen concentration areas.

19 Claims, 37 Drawing Sheets

METHODS AND SYSTEMS FOR NON-INVASIVE MEASUREMENT OF SOIL CHLORINE AND/OR NITROGEN CONTENT AND FOR DETECTING SUB-SURFACE CHLORINE OR NITROGEN-CONTAINING OBJECTS

REFERENCE TO RELATED APPLICATIONS

This application claims the benefit of U.S. Provisional Application No. 62/327,039, filed Apr. 25, 2016, which is incorporated herein by reference in its entirety.

BACKGROUND OF THE INVENTION

Field of Invention

The present invention relates generally to methods and portable devices for the non-invasive measurement of soil chlorine contamination and distribution. Portable devices of the present invention can also be used to detect chlorine-containing underground objects rapidly and on-site.

Background

Various techniques exist for characterizing elemental composition of a wide array of samples—from soil samples to luggage at airports—that do not destroy the samples. One such methodology utilizes measurement of gamma rays emitted from samples subjected to neutron radiation. For example, inelastic neutron scattering (INS) of fast neutrons from carbon-12 nuclei produce gamma rays that can be used to measure carbon content of soils (US Pat. App. 2002/0150194). Such approaches allow for analysis of large volumes with no sample preparation.

Contamination of soils with chlorine and chlorinated compounds can occur through multiple routes, including run-off from de-icing compounds from roadways and as by-products of industrial manufacturing processes. Polychlorinated hydrocarbons, such as carbon tetrachloride, chloroform, trichloroethylene, and tetrachloroethylene have been widely used as chemical intermediates, solvents for dry cleaning of clothing, in degreasing operations, and in a variety of other applications. Chlorinated hydrocarbons are very stable compounds and are relatively toxic at low levels. In some regions, the soil has become contaminated by these chlorinated hydrocarbons from sources such as disposal facilities, chemical spills, leaking storage tanks, and so forth.

The accumulation of chlorinated hydrocarbons in the soil poses a hazardous soil contamination problem. Moreover, the chlorinated hydrocarbons in the soil can be carried into groundwater sources by water percolating through the soil thus contaminating groundwater. As a result, pollution of soil and the subsequent pollution of groundwater by chlorinated hydrocarbons has become an important environmental concern that has stimulated the development of remediation or treatment systems for contaminated soils.

Additionally, chlorinated compounds such as trinitrochlorobenzene, ammonium perchlorate, and tetraaminecopper perchlorate are components of explosive ordinances, some of which are buried in soil on purpose and others buried as a method of disposal. Thus, the ability to detect chlorine contamination or chlorine-containing objects buried under soil quickly and remotely is desired.

The detection of chlorine in soil is currently achieved with the use of soil sampling and laboratory chemical analysis. This requires point sampling of the soil at specific soil depths of interest and careful soil processing of the samples to prepare them for chemical analysis in the laboratory. The soil samples have to be carefully handled to prevent cross contamination between samples. Due to the limits imposed from data collected from point sampling, many soil samples are required to be collected in order to assure accurate interpretation across topological spaces.

The laboratory analysis is difficult and expensive. The analysis can be done by either analyzing the soil chlorine content, as outlined by Adriano and Doner (Adriano and Doner, 1982. Bromine, Chlorine, and Fluorine. In: A. L. Page et al., (ed.) Methods of Soil Analysis. Part 2. Chemical and Microbiological Properties. $2^{nd}$ edition, Agronomy Monograph 9. Soil Science Society of America, Madison, Wis.), or by determining the concentration of specific compounds of interest, such as chlorinated hydrocarbons, as outlined in EPA Method 8121 (US EPA. 1994 available at www.epa.gov/sites/production/files/2015-12/documents/8121.pdf).

Similarly, equipment used to for the non-invasive measurement of chlorine may also be (with some modification) used to measure soil nitrogen content and the carbon/nitrogen ratio present in the soil. There are several agronomic applications in which these measurements are important—such as the nitrogen content of animal manures either present or potentially added to the soil and the amount of nitrogen present in compost. For manures, application rates for soil fertility are based on nitrogen content which can greatly vary and the instrument can be used to determine application rates for the manure. For the composting process, the carbon/nitrogen ratio of the compost is a critical factor not only for monitoring the progress of the composting process but also for determining the utility of the final product. Therefore, measuring the carbon/nitrogen ratio of compost is essential for composting facilities. However, analysis of compost carbon/nitrogen ratio is both expensive and time consuming.

Another application of the nitrogen measuring equipment is in the remediation of soil contamination by nitrogen-containing materials such as explosives. The ability of the system described herein to determine the carbon/nitrogen ratio of a material would potentially allow for the identification of an unidentified explosive without disturbing the material. Of particular interest would be identification of unexploded ordinance associated with military training grounds. The Department of Defense's (DoD) test and training ranges are a critical asset for the military. Maintaining these ranges is essential to enable troops to train in realistic circumstance at appropriate scales and to develop and test new weapons systems.

To address these issues, presented herein are systems and methods for detecting surface soil chlorine and nitrogen contamination as well as buried objects containing potentially harmful substances. Also provided herein are methods of detecting objects containing chlorine and nitrogen based on measuring the gamma responses from neutron irradiated samples.

SUMMARY OF THE INVENTION

Provided herein is a system for determining the presence or amount of chlorine or nitrogen in, or below, a testable surface. In one embodiment, the system contains: a neutron generator capable of producing pulsed neutron beams; a moderator positioned between the neutron generator and the testable surface; a gamma ray detector positioned to detect a gamma response from the testable surface when the neutron beam impinges thereon; an electronics block in electronic communication with the neutron generator and capable of operating the neutron generator; an additional electronics block in electronic communication with the gamma ray detector and capable of acquiring gamma spectra data during and between the pulsed neutron beams; and a computer system in electronic communication with at least one other component of the system. In some embodiments, the system also comprises a mobile chassis. In particular embodiments, the mobile chassis is in electronic communication with the computer system and movement of the mobile chassis is controlled by the computer system.

In some embodiments, the neutron generator is a deuterium-tritium generator. In still other embodiments, the computer system is in communication with one or more of the electronics blocks present in devices of the present invention. In additional embodiments, a system of the present invention also has gamma ray shielding positioned between the neutron generator and the gamma ray detector. In some embodiments, the gamma ray detector comprises a NaI(Tl) detector and the NaI(Tl) detector can be a cubic scintillator crystal with a volume of at least 2.45 dm$^3$. In some embodiments, the moderator is made of polyethylene and can be between four and six centimeters thick. In still other embodiments, the computer system is a laptop computer. In particular embodiments, the pulsed neutron beams produced by the neutron generator have a neutron energy of about 14.1 MeV. In common embodiments, the system is portable. The systems of the present invention can be used to test surfaces such as soil. In some embodiments, the electronics block in electronic communication with the gamma ray detector acquires gamma spectra between pulsed neutron beams produced by the neutron generator.

Further provided herein is a method for determining the presence, absence, or amount of chlorine or nitrogen, or below, a testable surface, having the steps of: 1) generating a pulsed neutron beam with a neutron generator from a point above a testable surface to a portion of, or under, the testable surface, where the neutron beam passes through a moderator to generate thermal neutrons; 2) inducing gamma ray emission from chlorine or nitrogen in or under a testable surface when the thermal neutrons impinge upon chlorine or nitrogen nuclei; 3) detecting the gamma ray emission with a gamma ray detector at discrete energy levels to provide an energy spectrum, and; 4) analyzing the energy spectrum based on known chlorine or nitrogen gamma ray energy levels thereby determining the presence or amount of chlorine or nitrogen in, or below, a testable surface.

In most embodiments, the presence, absence or amount of chlorine or nitrogen is determined by using the system described in the preceding paragraph. In particular embodiments, the testable surface is soil. In some embodiments, the neutron generator is a deuterium-tritium generator. In still other embodiments, the pulsed neutron beams have a neutron energy of about 14.1 MeV. In particular embodiments, the gamma ray emission is detected with a NaI(Tl) detector. In practicing the methods of the present invention, the presence, absence or amount of chlorine can be determined within one minute of generating the first neutron beam. In a particular embodiment, the neutron generator and the detector are mounted on a mobile chassis and the chassis moves from one location to another and repeats the steps of the process to determine the presence, absence, or amount of chlorine at the second location.

In a further embodiment, one or more additional locations are analyzed for the presence, absence, or amount of chlorine. In some embodiments, the chassis is caused to move by a computer system in electronic communication with the chassis. Utilizing this multiple location analysis embodiment, the presence, amount, or absence of chlorine or nitrogen is determined within one minute of generating the first neutron beam at one or more of the additional locations.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The novel features of the invention are set forth with particularity in the claims. Features and advantages of the present invention are referred to in the following detailed description, and the accompanying drawings of which:

DETAILED DESCRIPTION OF THE INVENTION

Figure 1A:
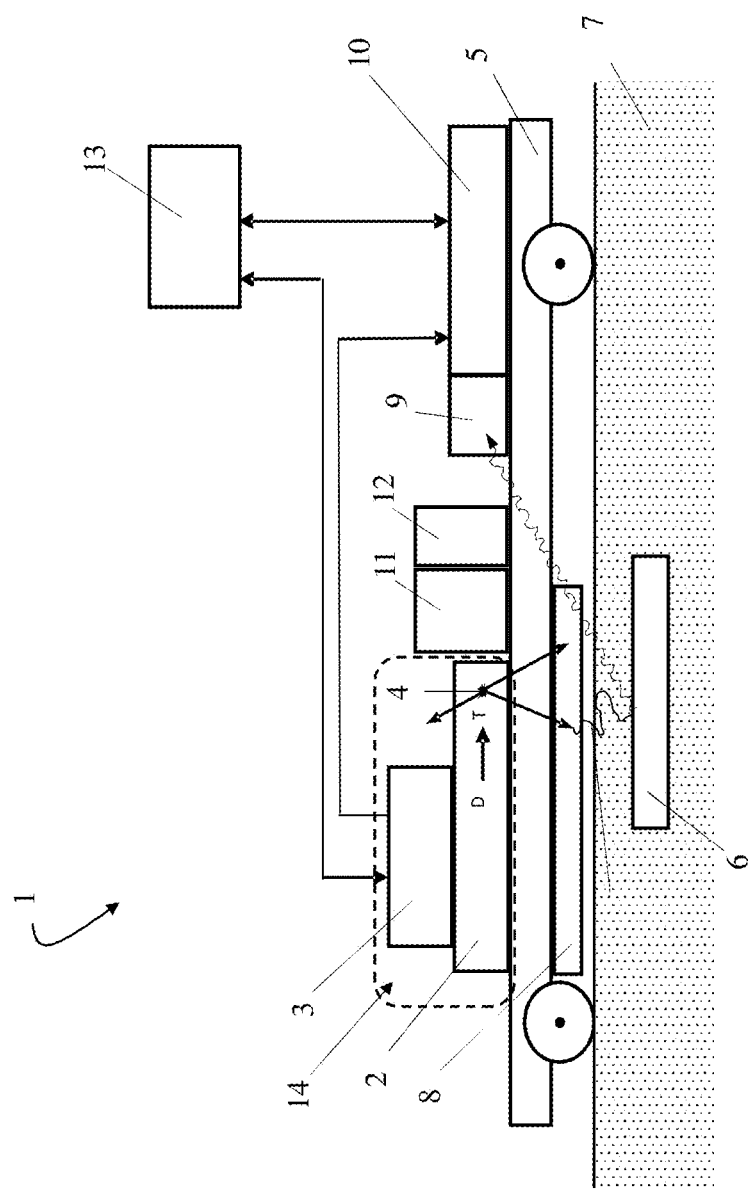
FIG. 1A depicts a device for detecting chlorine or nitrogen content of substrates and objects below a substrate surface.

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

The terms "about", "approximately", and variations thereof are defined as plus or minus ten percent of a recited value. For example, about 1.0 g means from a range of 0.9 g to 1.1 g, or any particular value within the range.

As used in the specification and claims, use of the singular "a", "an", and "the" include plural references unless the context clearly dictates otherwise.

Overview

Detailed herein, is a system for measuring or detecting soil surface chlorine or nitrogen contamination and buried objects containing chlorine. Typically, a system of the present invention irradiates a surface and/or sub-surface or object(s) to be analyzed with neutrons. Different gamma lines appear due to the interaction of neutrons within the nuclei of a studied surface/object (including chlorine nuclei) as well as within the nuclei of surrounding materials, due to inelastic neutron scattering (INS) and thermal neutron capture (TNC). In preferred embodiments, a neutron generator is used in the system to produce fast neutrons with energy of 14.1 MeV. A gamma detector is used in the system for registration of gamma rays. Neutron propagation in studied surfaces/objects and in other materials (e.g., the components of the system itself or other non-chlorine components of the environment) runs to their moderation to thermal energy due to elastic neutron scattering and INS with nuclei of the materials.

The overall detected gamma spectra generated using a system of the present invention in such a manner is very strong and continuous with practically no structure due to INS and Compton scattering of generated gamma rays from the materials. Resulting gamma lines of interest do not stand out against the background of such continuous gamma spectra. The utilization of a moderator (material with low Z) in a system of the present invention between a neutron source and the studied surface/object converts fast neutrons to mainly thermal neutrons prior to their impinging upon the studied surface/object. Subsequently, the interaction of thermal neutrons with the nuclei within the studied surface/ object increases the TNC produced gamma lines, including chlorine TNC gamma lines of chlorine of which the strongest line has an energy of 1164 keV. However, gamma rays resulting from INS from nuclei within the moderator and surrounding equipment material still does not allow separation of the desired gamma lines in the spectra.

However, the systems disclosed herein are capable of comparing the separated acquisition gamma rays produced during the neutron pulses and between neutron pulses. This separated acquisition, typically performed by one or more of the electronic components of the systems, is used to decrease the continuous gamma background and separate gamma lines in the spectra.

Thus, in preferred embodiments, at least two gamma spectra are acquired during measurement or detection of chlorine and/or nitrogen: INS gamma spectra acquired during the neutron pulses and TNC gamma spectra acquired between the neutron pulses. The TNC gamma spectra provides a set of separate gamma lines with lower continuous background, while the INS spectra provides continuous background with practically no structure.

Figure 3:
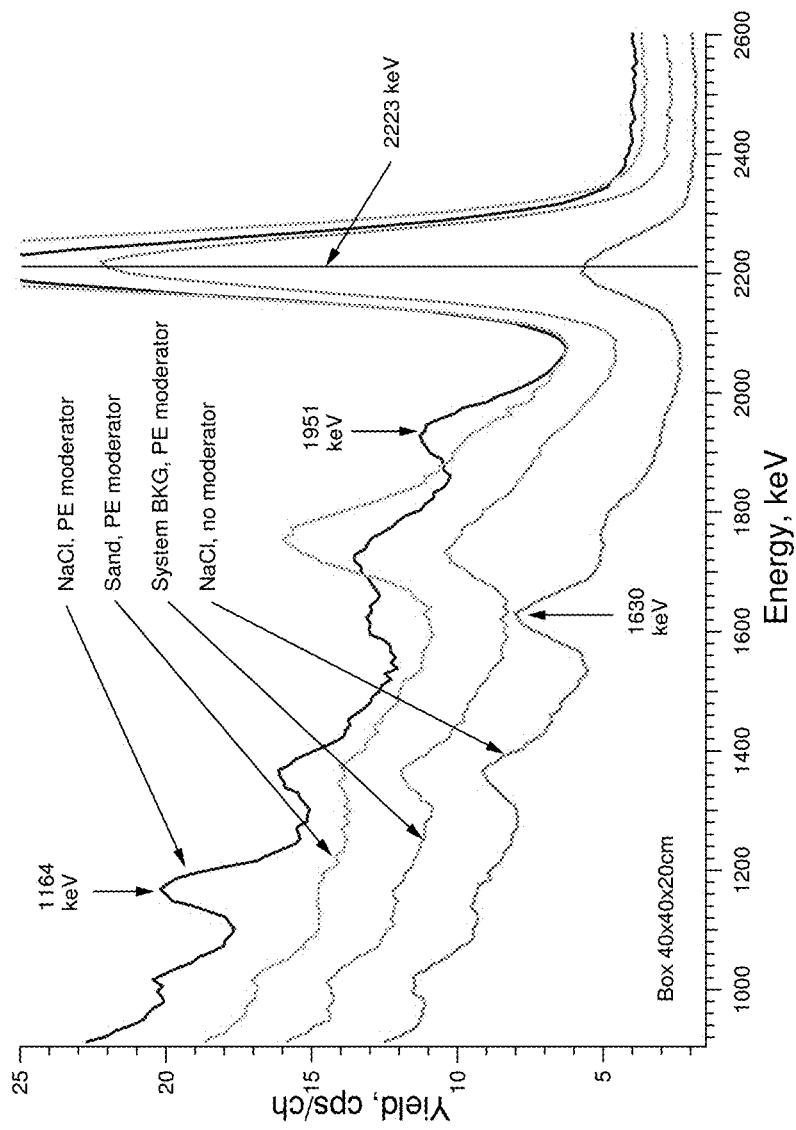
FIG. 3 provides a graph depicting gamma ray spectra for sand and for a NaCl sample measured between neutron pulses by a system of the present invention working in pulse mode with and without a moderator.

For the purpose of this application, a "gamma ray spectra" is defined as a distribution of the gamma rays intensities at different energies detected by a gamma detector. For example, FIG. 3 shows a gamma ray spectra for sand and for a NaCl sample measured between neutron pulses by a system of the present invention working in pulse mode with and without a moderator.

For the purpose of this application, a peak is defined as an increase in the number of counts detected as compared to the background. For example, FIG. 3 shows a spectra where the counts per second (CPS) display a clear peak with a centroid at about 1164 keV for the sample were chlorine was present.

Note that the Chlorine and Nitrogen are measured primarily with TNC while the carbon is measured primarily with INS. Both the Nitrogen and the Chlorine are helped with the use of a moderator, but the moderator interferes with the measurement of carbon. The C/N ratio can be measured without the moderator because, even though it hinders the detection of the N, both Carbon and Nitrogen can be measured at the same time. Additionally, it is easier to measure the C/N ratio than it is nitrogen content alone.

Chlorine

The gamma lines connected with chlorine can be found in the TNC gamma spectra of surfaces/objects with chlorinated compounds and can be measured by a system of the present invention. Due to the relatively high cross-section of TNC by chlorine nuclei (43 b), the intensity of these lines is sufficient to measure chlorine even at low chlorine content in samples. The strongest of these lines with energy 1164 keV can be used as an analytical line in accordance with the present invention.

In a particular embodiment, a system of the present invention utilizes a portable pulse D-T neutron generator (neutron energy 14.1 MeV), NaI(Tl) gamma detector (scintillator volume of at least 2.4 dm$^3$), polyethylene moderator (5 cm thickness), construction framework and shielding that protects the gamma detector against direct neutron flux. Any neutron generator or neutron pulse source known in the art can be utilized, however, accelerator based neutron sources, such as deuterium-deuterium (D-D) and deuterium-tritium (D-T) fusion neutron generators and others that allow for electronic control of neutron emission are preferred. D-T neutron generators are particularly preferred in practicing the present invention. Such generators can be pulsed (i.e., turned off and on for various lengths), providing electronic control of neutron emission. Such control allows for the separation of gamma ray signatures due to TNC emitted from materials being analyzed from other gamma lines. Neutron generators producing thermal neutrons can be utilized in some embodiments.

In addition to neutron generators, systems of the present invention have one or more gamma ray detectors. Any gamma ray detector known in the art can be utilized in practicing the inventions disclosed herein, but preferred detectors are suitable for operation in mixed radiation fields where neutrons and gamma rays are present. Also preferably, a gamma ray detector is capable of energy resolution that allows the system to resolve peaks of interest is utilized. Some non-limiting examples of detectors include, but are not limited to high purity germanium detectors (HPGe) and scintillation detectors (NaI(Tl), $Bi_4Ge_3O_{12}$, $LaBr_3(Ce)$).

In some embodiments of the present invention, a neutron moderating material is utilized to convert fast neutrons produced by a neutron generator, turning them into thermal neutrons. Any moderator known in the art can be utilized including, but not limited to water, heavy water, graphite, beryllium, beryllium oxide, high-density polyethylene and polyethylene. In preferred embodiments, the moderator comprises polyethylene. In systems of the present invention, the moderator material is preferably positioned between the neutron generator and the sample to be tested. Moderator material thickness can be modified in practicing variations of the present invention, for example, a moderator can be 0.5 cm, 1.0 cm, 1.5 cm, 2.0 cm, 2.5 cm, 3.0 cm, 3.5 cm, 4.0 cm, 4.5 cm, 5.0 cm, 5.5 cm, 6.0 cm, 6.5 cm, 7.0 cm, 7.5 cm, 8.0 cm, 8.5 cm, 9.0 cm, 9.5 cm, 10.0 cm, 10.5 cm, 11.0 cm, 11.5 cm, 12.0 cm, 12.5 cm, 13.0 cm, 13.5 cm, 14.0 cm, 14.5 cm, 15.0 cm, 15.5 cm or more centimeters thick.

Shielding is utilized in most embodiments and protects the gamma ray detector from direct targeting by neutrons produced by a neutron generator and/or provides protection to vulnerable components of the system (e.g., electronics) and human operators of the system. Shielding size and material can be modified to fit the geometry of a system, such that the shielding separates the neutron source from, for example, the gamma ray detector or human operator. Thus, shielding materials can be formed to any configuration desired, whether by directly shaping solid materials, or providing a shaped container for liquid shielding materials. Any neutron-gamma shielding material known in the art can be utilized in practicing the present invention including, but not limited to, borated polyethylene, water, heavy water, lead, boron carbide and enriched lithium fluoride. Furthermore, some embodiments of the present invention include multi-layer shielding (2 layers, 3 layers, 4 layers, or more layers). Such multi-layer configurations can include layers of the same material (e.g., two or more lead layers) or layers of different materials (e.g., at least one lead layer and at least one water layer).

Generally, the systems described herein to carry out measurements of chlorine content of samples consist of a neutron source, a gamma detector, and construction and shielding materials. Neutron generators produce neutrons due to the fusion nuclear reactions D-D (deuterium-deuterium) or D-T (deuterium-tritium). Typically, the use of a neutron generator is preferred over systems utilizing an isotope source (from a radiation safety point of view) because no radiation is produced when the generator is turned "off." D-D generators produce 2.5 MeV neutrons while D-T generators produce 14.1 MeV neutrons. The neutron flux of D-T generators is more than that of D-D generators (at the same power) thus, the use of a D-T generator for measurement is typically preferred in practicing the invention. The emission of gamma rays from chlorine containing material irradiated with fast neutron flux occurs due to a neutron-chlorine nuclei interaction. Some of these gamma rays can be used to detect chlorine. Chlorine associated gamma rays can appear due to both inelastic neutron scattering (INS) and thermal neutron capture (TNC). Preferred embodiments of the present invention utilize TNC when detecting chlorine-containing materials.

Fast neutrons moderate to thermal energy upon penetrating the moderator, and the thermal neutron flux interacts with surface chlorine contamination (such as in soil) or buried objects containing chlorine. Due to TNC by chlorine nuclei, several gamma lines appear (strongest at 1164 MeV). Gamma spectra acquisition can take place at any time following a neutron pulse from the generator, or can be acquired constantly. In preferred embodiments, gamma spectra acquisition takes place between neutron pulses. Aside from the spectra measurement (gamma-ray yield in count number per keV or per channel versus gamma ray energy), surface chlorine contamination or buried objects containing chlorine can be detected by checking the count rate in channels around the 1164 MeV peak centroid for a short period (~30 s). The amount, presence or absence of surface chlorine, sub-surface chlorine and buried objects containing chlorine can be detected within 20 seconds, 30 seconds, 40 seconds, 50 seconds, 60 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, 30 minutes, 31 minutes, 32 minutes, 33 minutes, 34 minutes, 35 minutes, 36 minutes, 37 minutes, 38 minutes, 39 minutes, 40 minutes, 41 minutes, 42 minutes, 43 minutes, 44 minutes, 45 minutes, 46 minutes, 47 minutes, 48 minutes, 49 minutes, 50 minutes, 51 minutes, 52 minutes, 53 minutes, 54 minutes, 55 minutes, 56 minutes, 57 minutes, 58 minutes, 59 minutes, or 60 minutes utilizing devices of the present invention.

In some embodiments, the system of the present invention includes a mobile platform, allowing the system to be moved from one location to another. Moving such systems can be performed manually (e.g., by placing the system at a particular spot to be analyzed), can be performed remotely by an operator to scan a particular area, can be performed remotely by a computer component pre-programmed with a search grid, can be performed remotely by a computer component programmed to guide the device to higher concentrations of chlorine after detection has begun, or any other guidance mechanism known in the art. Those of skill in the art will recognize that there are multiple ways of moving and/or controlling mobile devices of the present invention.

The chlorine detection methodologies described herein can be used to survey potentially contaminated areas in a variety of ways. In some embodiments, a quasi-scanning regime is utilized, whereby the mobile system stops at a given interval before moving onto the next location to be surveyed. For example, a system of the present invention scanning for surface chlorine contamination can stop over a section of the test area (e.g., an agricultural field) to take a measurement for thirty seconds before moving to the next location. The time spent analyzing a particular location can be modified based on the required minimal detectable level of chlorine contamination or mass of buried chlorinated object. Thus, a mobile device of the present invention can scan a particular area for 30 seconds, 40 seconds, 50 seconds, 60 seconds, 70 seconds, 80 seconds, 90 seconds, 100 seconds, 110 seconds, 120 seconds, 130 seconds, 140 seconds, 150 seconds, 160 seconds, 170 seconds, 180 seconds, 190 seconds, 200 seconds, 210 seconds, 220 seconds, 230 seconds, 240 seconds, 250 seconds, 260 seconds, 270 seconds, 280 seconds, 290 seconds, 300 seconds, 310 seconds, 320 seconds, 330 seconds, 340 seconds, 350 seconds, 360 seconds, 370 seconds, 380 seconds, 390 seconds, 400 seconds, 410 seconds, 420 seconds, 430 seconds, 440 seconds, 450 seconds, 460 seconds, 470 seconds, 480 seconds, 490 seconds, 500 seconds, 510 seconds, 520 seconds, 530 seconds, 540 seconds, 550 seconds, 560 seconds, 570 seconds, 580 seconds, 590 seconds, 600 seconds, 600 seconds, 610 seconds, 620 seconds, 630 seconds, 640 seconds, 650 seconds, 660 seconds, 670 seconds, 680 seconds, 690 seconds, 700 seconds or more before moving onto the next area to be analyzed. Utilizing the systems and methodologies of the present invention it is possible to detect the presence or amount of chlorine and chlorine-containing objects at the surface of a scanned area or 0.1 cm, 0.2 cm, 0.3 cm, 0.4 cm, 0.5 cm, 0.6 cm, 0.7 cm, 0.8 cm, 0.9 cm, 1.0 cm, 1.5 cm, 2.0 cm, 2.5 cm, 3.0 cm, 3.5 cm, 4.0 cm, 4.5 cm, 5.0 cm, 5.5 cm, 6.0 cm, 6.5 cm, 7.0 cm, 7.5 cm, 8.0 cm, 8.5 cm, 9.0 cm, 9.5 cm, 10.0 cm, 10.5 cm, 11.0 cm, 11.5 cm, 12.0 cm, 12.5 cm, 13.0 cm, 13.5 cm, 14.0 cm, 14.5 cm, 15.0 cm, 15.5 cm, 16.0 cm, 16.5 cm, 17.0 cm, 17.5 cm, 18.0 cm, 18.5 cm, 19.0 cm, 19.5 cm, 20.0 cm, 20.5 cm, 21.0 cm, 21.5 cm, 22.0 cm, 22.5 cm, 23.0 cm, 23.5 cm, 24.0 cm, 24.5 cm, 25.0 cm, 25.5 cm or more centimeters beneath the surface.

Figure 11:
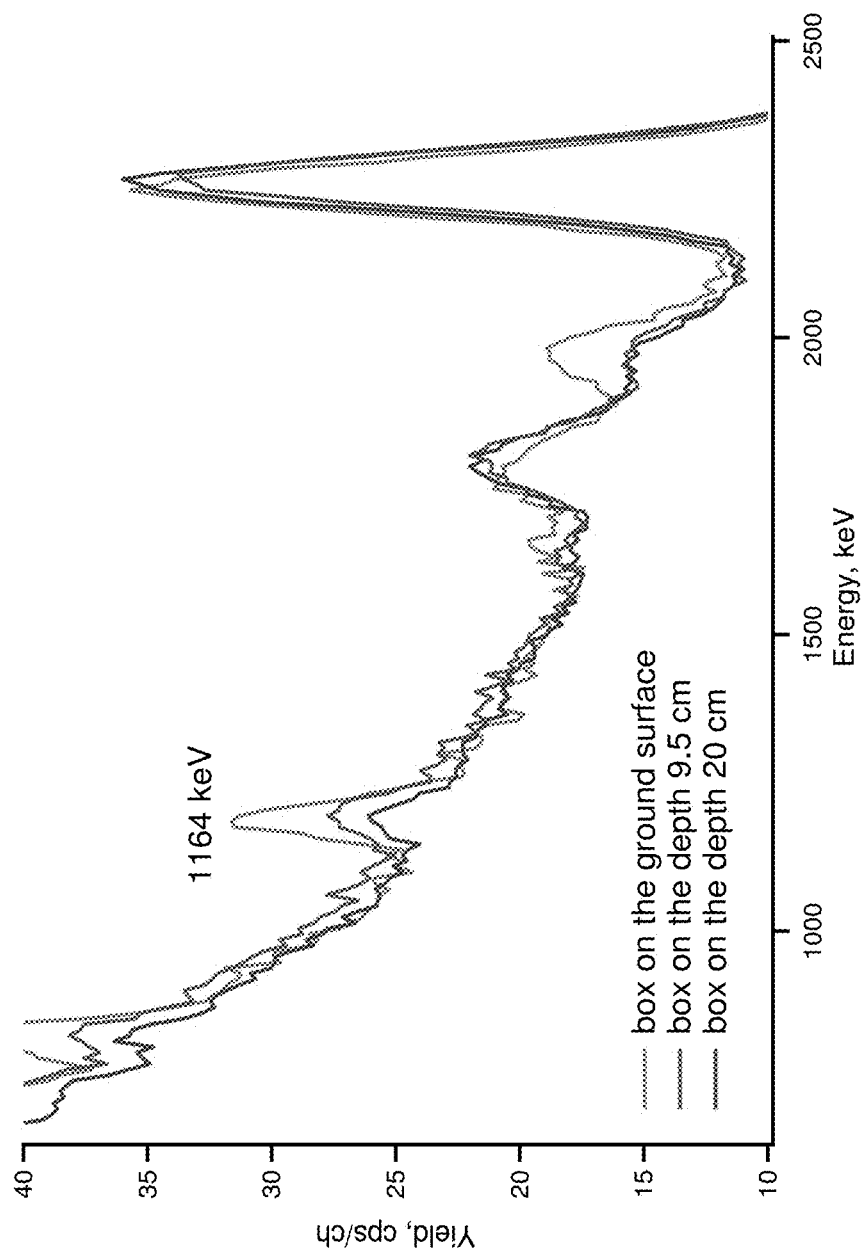
FIG. 11 provides a graph illustrating the gamma spectra of a 6.5 kg NaCl sample buried in soil at different depths measured between neutron pulses for a system of the present invention working in pulse mode with a PE moderator.

Minimal detectable level (MDL) for measurement or detecting surface or sub-surface chlorine contamination and buried objects containing chlorine can be estimated as next $$MDL = \frac{4.65 \cdot \sqrt{\frac{BkgPa1164}{LT}}}{s}$$

where BkgPa1164 is background under peak area with centroid 1164 keV in cps, LT is the life time of measurement $$LT = WT \cdot \left[1 - \left(\frac{DC}{f \cdot 100} + 2 \cdot 10^{-6}\right) \cdot f \cdot \left(1 - \frac{DT}{100}\right)\right]$$

where WT is wall time of measurement, s, f, Hz, and DC, %, are frequency and dirty cycle of neutron generator work, DT, %, is dead time of work of scintillation detector, s is sensitivity of system to chlorine, $$s = \frac{Pa1164}{m}$$

where Pa1164 peak area with centroid 1164 keV in cps, m is value of chlorine in studied object (in kg Cl per square meter if surface contamination is measured, or in kg Cl if chlorine content buried object is measured or detected). The calculations of Pa1164 and BkgPa1164 from these spectra and estimation of MDL values for different measurement wall times were done. For system of the present invention with one detector for considered example, the wall time should be 30 s to have the MDL equal to 1.2 kg Cl m², while the wall time should be 5 min to have the MDL equal to 0.4 kg Cl m². Note that, by increasing the number of detectors and neutron flux, the sensitivity can be increased and the corresponding MDL for the measurement time will decrease. For instance, increasing the number of detectors to three and neutron flux by 10 times will increase Pa1164 and BkgPa1164 approximately 30 times. This gives a MDL equal to 0.22 kg Cl/m² for a 30 s measurement and a MDL equal to 0.07 kg Cl/m² for a 5 min measurement. Another example. The gamma spectra of a 6.5 kg NaCl sample buried in soil measured between neutron pulses for a system of the present invention working in pulse mode with a PE moderator at different burial depths are demonstrated in FIG. 11. The calculations of Pa1164 and BkgPa1164 from these spectra and estimation of MDL values for different measurement times with current and advanced (3 detectors, neutron flux $10^8$ n/s) modification are represented in Table 1.

TABLE 1

Depth and MDL for Chlorine detection and measurement.

| Depth of sample, cm | MDL for 30 s measurement, kg Cl | | MDL for 5 min measurement, kg Cl | |
|---|---|---|---|---|
| | Current modification | Advantage modification | Current modification | Advantage modification |
| 0 | 1.5 | 0.3 | 0.5 | 0.1 |
| 9.5 | 3.8 | 0.7 | 1.2 | 0.2 |
| 20 | 5.5 | 1.0 | 1.7 | 0.3 |

Figure 1B:
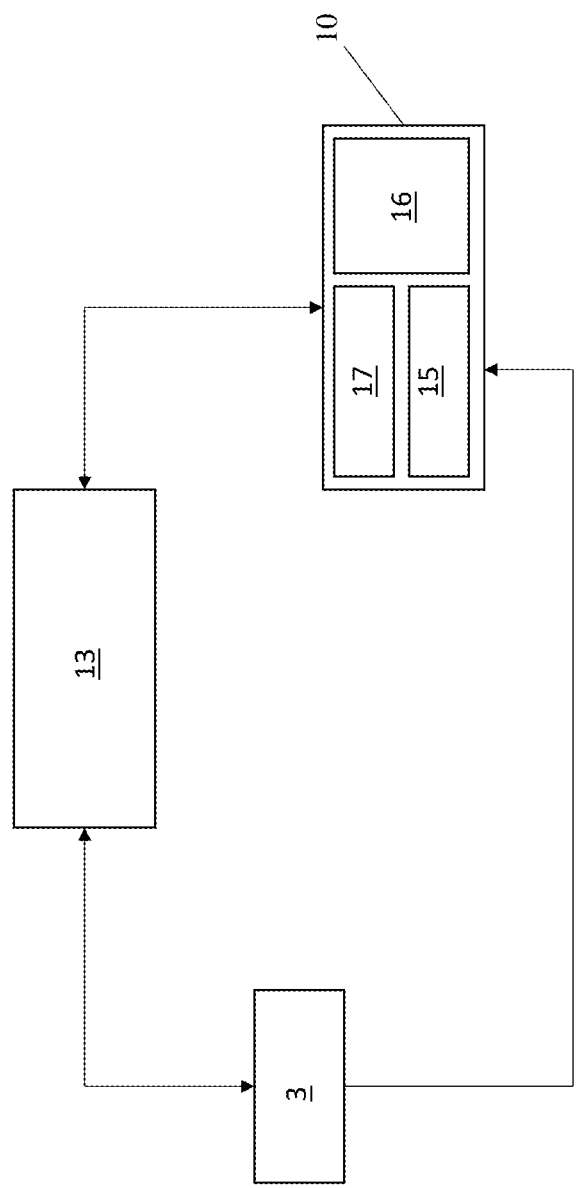
FIG. 1B is an illustrative connection and control scheme for the electronics portion of a device of the present invention.

Referring to FIG. 1.A and FIG. 1.B, a detection system 1 according to the present invention for detecting soil surface chlorine contamination or buried objects containing chlorine is a mobile, deployable field unit. The system 1 comprises a neutron generator assembly 14, comprising an accelerator tube 2 and a neutron generator controller 3 for controlling the flux parameters and other aspects of the neutron generator 14, a moderator 8 for converting fast neutrons into thermal neutrons, a gamma ray detector 9, a gamma ray detector processor/controller 10 connected the neutron generator controller 3 for coordination of detection, shielding 11, additional or different shielding 12, a monitoring/controlling computer system 13, and a moving chassis 5. The neutron generator controller 3, the gamma ray detector processor/controller 10 and the monitoring/controlling computer system 13 can be integrated as one unit, or may be separate units as shown in FIG. 1.A.

The system 1 neutron generator assembly 14 is preferably a D-T generator for producing a fast neutron flux and preferably has an output of about $10^7$ n/s, a pulse width of 50 μs and a repetition rate of $5·10^3$ pulses/s. The neutron generator assembly 14 includes the neutron generator controller 3 that controls when neutrons are produced by the accelerator tube 2. A suitable D-T neutron generator, for example, is an MP320 model generator (ThermoScientific, Inc.) or a Model No. A325 generator (MF Physics Corp.), but any suitable neutron generator known in the art can be utilized. A pulse of accelerated deuterons hits a tritium saturated target 4 present within the accelerator tube 2. As a result of the deuteron-tritium nuclear reaction, 14.1 MeV neutron flux is isotropically produced. The fast neutron flux directly irradiates a chlorine containing object 6 and analyzed substrate 7 or passes through a moderator 8 converting the fast neutrons to thermal neutrons.

The interaction of fast neutrons with the studied object will mainly produce the gamma lines listed in Table 2 while the interaction of thermal neutrons with the studied object will mainly produce the gamma lines listed in Table 3 (cells containing two gamma ray energies indicates that the lines overlap in the gamma spectra when measured using a NaI(Tl) detector). The gamma detector 9 converts the gamma rays to electrical signals allowing for measurement of the gamma flux spectra. In preferred embodiments, the gamma detector 9 is a NaI(Tl) detector that consists of a cubic scintillator crystal with a volume of at least 2.45 dm³. As best shown in FIG. 1.B, a gamma ray detector processor/controller 10 associated with the gamma detector 9 preferably comprises a photomultiplier and preamplifier 17, split electronics processing system 15 (that separate the concurrent spectra acquisition during the neutron pulse and between pulses), and a multi-channel analyzer (MCA) 16.

TABLE 2

Main neutron-chlorine INS processes and associated gamma lines.

| Energy, MeV | Nuclear Reaction | Production cross-section, mb/sr at 90° |
|---|---|---|
| 1.21 | Cl35(n,n')Cl35* | 7.6 |
| 1.76 | Cl35(n,n')Cl35* | 6.5 |
| 2.13 | Cl35(n,d)S34* | 17.1 |
| 2.7 | Cl35(n,n')Cl35* | 5.4 |
| 3.08 | Cl37(n,n')Cl37* | 3.0 |
| 3.17 | Cl35(n,n')Cl35* | 5.8 |

TABLE 3

Energies and intensities of prompt gamma rays at neutron capture by Cl-35 (Strongest transition Eγ = 1164.86 keV Iγ (max) = 26.82%).

| Gamma ray energy, keV | Intensity, Iγ/Iγ (max), % |
|---|---|
| 786.3 | 38.37 |
| 788.4 | 60.81 |
| 1164.86 | 100 |
| 1170.94 | 20.43 |
| 1601.06 | 13.61 |
| 1951.13 | 71.03 |
| 1959.34 | 46.01 |
| 2863 | 20.40 |
| 3061 | 12.64 |
| 4979.89 | 13.83 |
| 5715.36 | 20.40 |
| 6110.93 | 73.97 |
| 6619.73 | 28.41 |
| 6627.94 | 16.44 |
| 7414 | 36.91 |
| 7790 | 29.87 |

Shielding 11 and 12 is preferably mounted between the accelerator tube 2 of the neutron generator assembly 14 and the gamma detector 9 in order to protect the gamma detector 9 against direct neutron irradiation. Shielding 11 and 12 can comprise the same material, or different materials. For example, in a particular embodiment, shielding 11 comprises water and shielding 12 comprises lead. In some instances, shielding 11 and 12 are integrated as a single unit.

The neutron generator assembly 14 can be operated by the monitoring/controlling computer system 13 which is in electronic communication either directly or wirelessly with one or more components of the system 1, including the neutron generator assembly 14. The gamma ray detector processor/controller 10 typically processes gamma ray data and communicates with other elements of the system 1. The gamma ray detector processor/controller 10 may perform both processing and/or controlling functions. The gamma spectra can be acquired during neutron pulses (gamma rays from INS, TNC, and background), between neutron pulses (gamma rays from TNC and background), or continuously (gamma rays from INS, TNC, and background).

The different spectra types are acquired by the MCA 16 which is in electronic communication with the computer system monitoring/controlling 13. In preferred embodiments, monitoring/controlling computer system 13 is a laptop computer with software capabilities to receive, interpret and/or present collected data. The monitoring/controlling computer system 13 may perform both monitoring and/or controlling functions. In some embodiments, monitoring/controlling computer system 13 controls the whole system.

The neutron generator controller 3 can (itself) be controlled by the software in the monitoring/controlling computer system 13. The split electronics processing system 15 is connected to the output signal from the neutron generator, which times the beginning and end of the neutron pulse, and governs the MCA 16 to acquire the spectra in one (during the neutron pulse) or another (between the pulses) part of the memory. In the case of the continuous neutron generator working regime, no signal goes from the neutron generator controller 3 to the split electronics processing system 15, and only one spectrum is acquired. The gamma ray detector processor/controller 10 is connected through a USB port to the monitoring/controlling computer system 13. The computer software controls the electrical parameters of the photomultiplier with preamplifier 17 and MCA 16, and governs the spectra acquisition.

Figure 2:
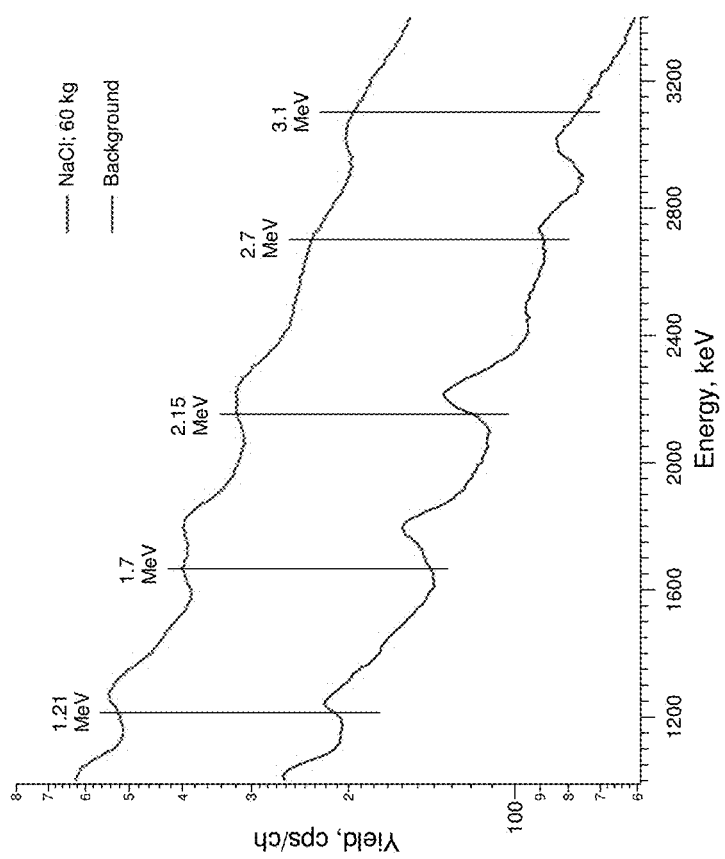
FIG. 2 provides a graph depicting gamma ray spectra for background and for a NaCl sample measured by a system of the present invention working in continuous mode without a moderator.

Upon neutron irradiation, the analyzed substrate 7 (e.g., potentially chlorine-contaminated soil) and/or the buried object 6 and the construction material surrounding the neutron generator (body of the generator, chassis etc.) produce large amounts of gamma rays due to both INS and TNC. Due to the high background level of the gamma rays entering the detector, it can be difficult to extract a useful signal for the studied object. FIG. 2 compares the background with a NaCl spectra acquired by the system without a moderator 8. The results show some changes in gamma peak range are displayed, but poor resolution limits peak recognition confidence.

The gamma spectra of NaCl, sand, and background measured in the TNC mode with and without a moderator are shown in FIG. 3. Compared to the system background spectrum, the spectrum labeled "NaCl, no moderator" has only one dominant peak with a centroid around 1630 keV. According to Engesser et al. (1967), this peak is due to Na-23 in NaCl. Smaller peaks unsuitable for analytical determination of chlorine were near some of the peak positions listed in Table 3. To increase the effect of the thermal neutron capture process, conversion of fast neutron flux to thermal neutron flux was achieved using a moderator. The TNC spectrum for ~50 kg of NaCl was measured with a polyethylene moderator; a fragment of this spectra is shown in FIG. 3 (labeled "NaCl, PE moderator"). Several peaks with centroids around the positions listed in Table 3 were observed. The dominant peaks at 1164 keV and 1951 keV are labeled in FIG. 3. The strongest peak (1164 keV) can be used for chlorine determination.

Figure 4:
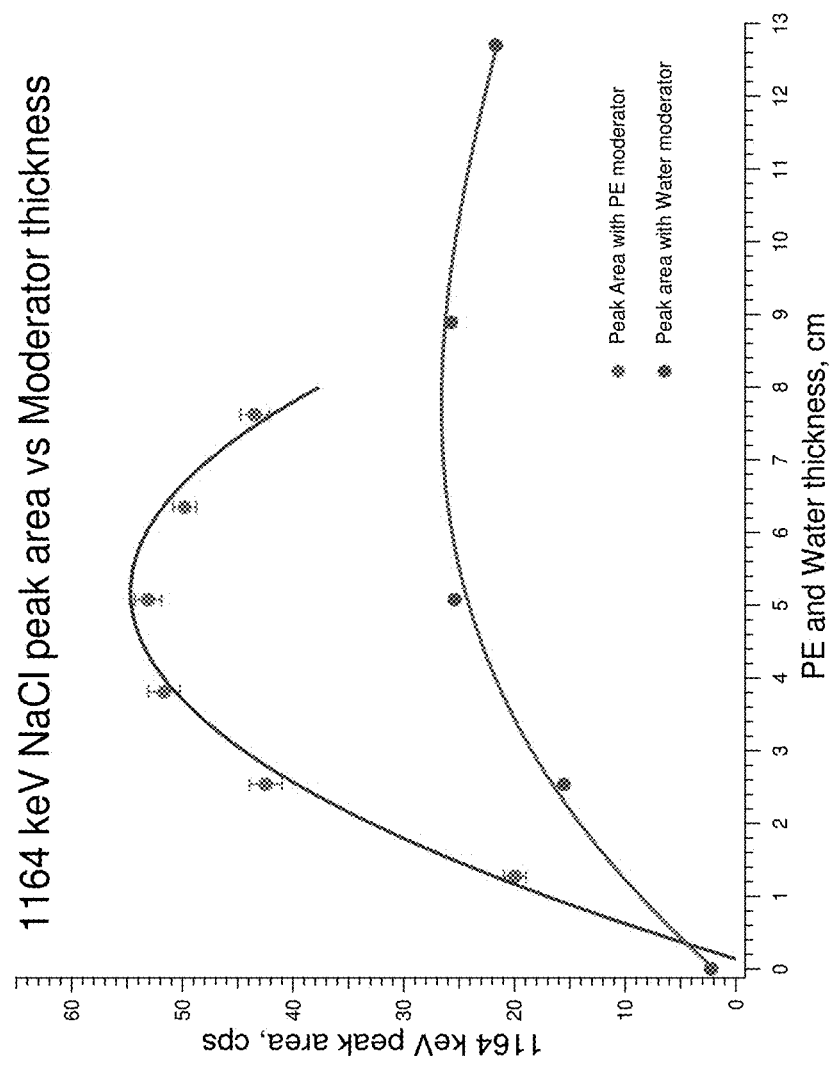
FIG. 4 provides a graph depicting the dependencies of the 1164 keV peak area in the gamma ray spectra of a NaCl sample measured between neutron pulses for a system of the present invention working in pulse mode comparing different moderator thicknesses of water and polyethylene moderators (PE).
Figure 5:
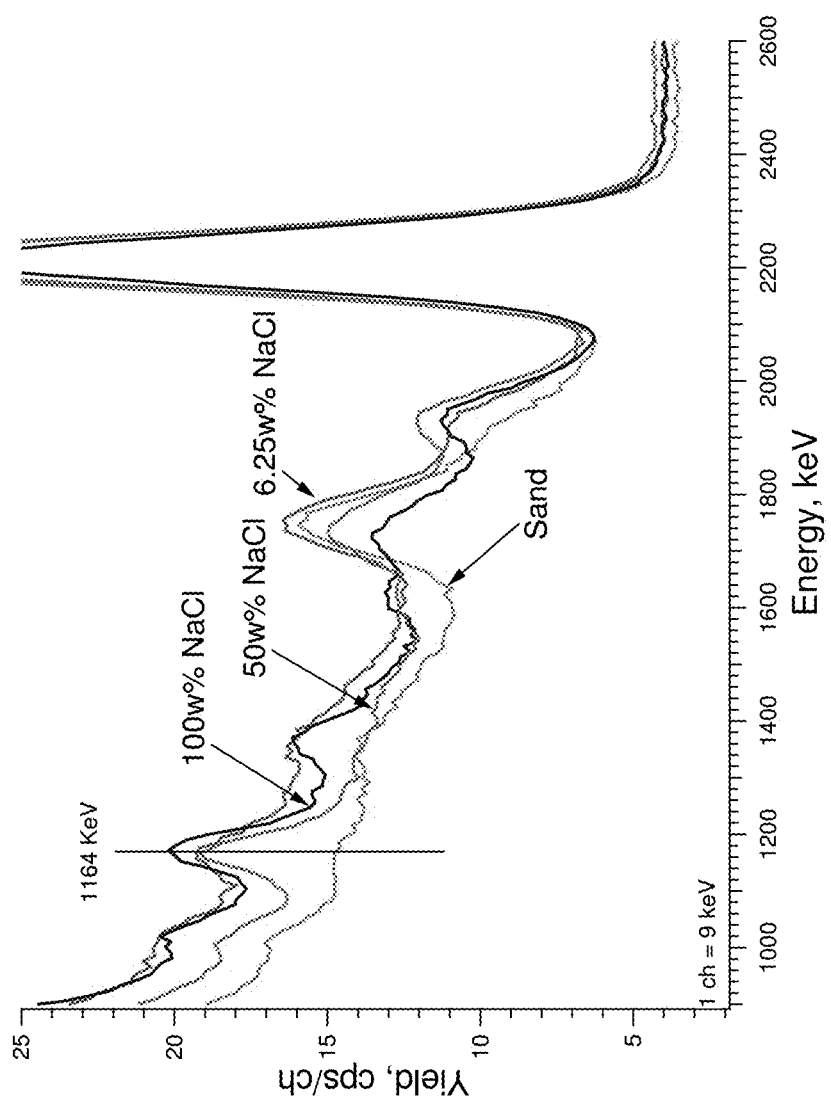
FIG. 5 provides the gamma spectra of a sand-salt mixture measured between neutron pulses for a system of the present invention working in pulse mode with a PE moderator (salt content is shown on the graph).

To optimize the moderator type and thickness, dependence of the 1164 keV peak area versus moderator thickness was investigated. Water and polyethylene were available for this testing, and measurement results are presented in FIG. 4. As shown in FIG. 5, a polyethylene moderator is preferable for the chlorine 1164 keV peak measurement. The optimal polyethylene moderator thickness for our experimental conditions was ~5 cm. This moderator (4 polyethylene sheets with a thickness of 1.25 cm and an area of 61 cm×61 cm) was used for further measurements.

Having described the invention in general, below are examples illustrating the generation and efficacy of the invention. Neither the examples, nor the general description above should be construed as limiting the scope of the invention.

EXAMPLES

Figure 7:
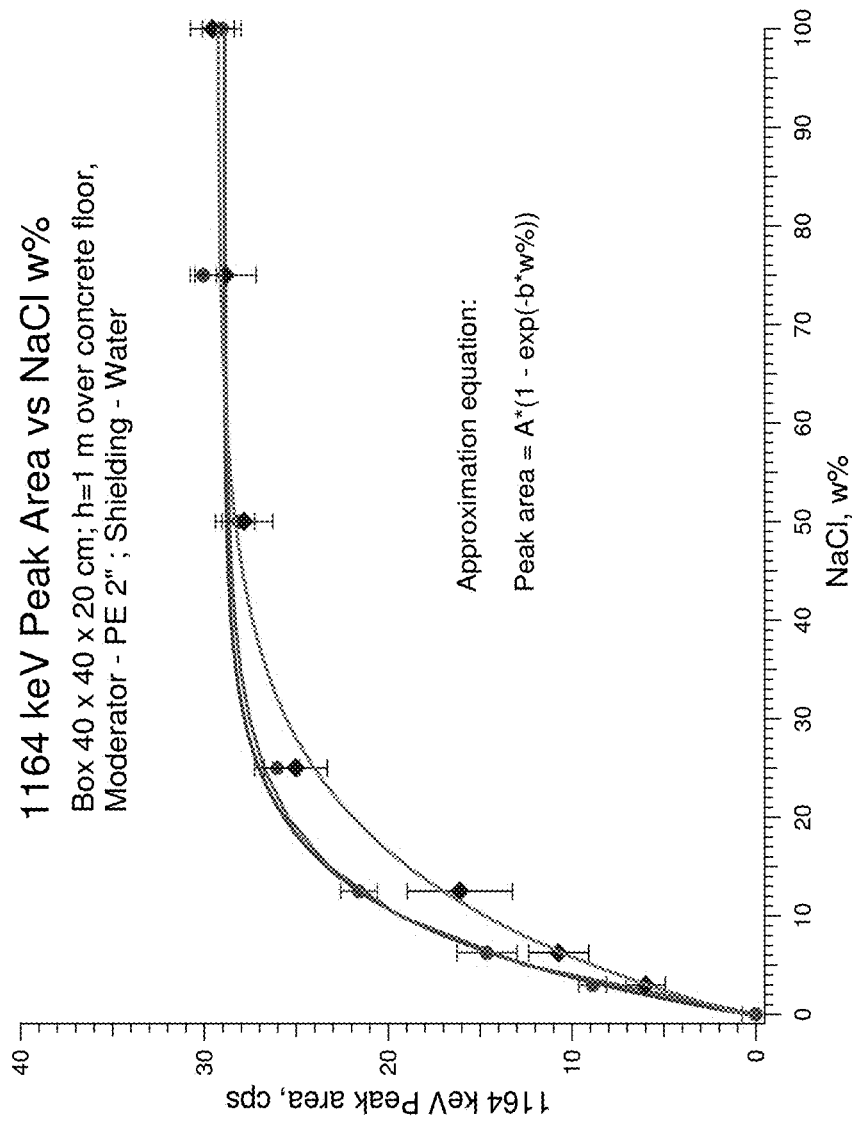
FIG. 7 provides a graph illustrating the 1164 keV peak area vs NaCl weight percent in sand-salt mixtures; red points and approximation lines are experimental; green points and approximation line are a Monte-Carlo simulation; and the blue line is a model (Eq. 3); all data are normalized at the saturation level for the experiment.

To study the effect of chloride content on the 1164 keV peak area, the TNC spectra were measured for different salt-sand mixtures (i.e., NaCl content of 3.1, 6.2, 12.5, 25, 50, 75 and 100 weight %) in boxes measuring 40 cm×40 cm×20 cm. As shown in FIG. 5, the value of the peak area with a centroid at 1164 keV changed with chloride content. The dependence of the 1164 keV peak area with chloride content is shown in FIG. 7 (red points and line). The value of the 1164 keV peak area increased as NaCl content increased, reached a level of saturation at ~40 w % NaCl, and did not change with additional NaCl.

Figure 6:
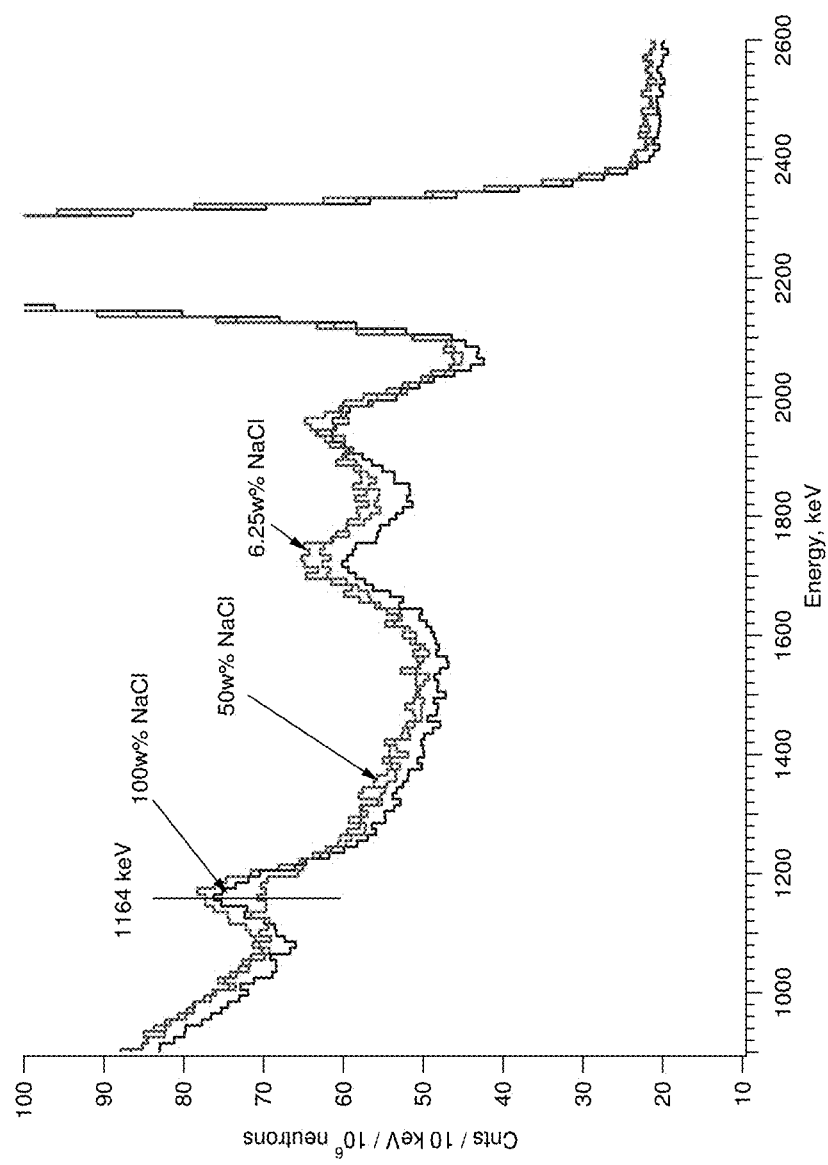
FIG. 6 provides a graph of a Monte-Carlo simulation (Geant4) gamma spectra of sand-salt mixtures with 6.25, 50, and 100 weight percent of NaCl.

A TNC Monte-Carlo simulation (using Geant4 toolkit) of the sand-salt mixture with a polyethylene moderator was also conducted. TNC simulations were done by inactivating the Inelastic Scattering physics command in the simulation code. Examples of the simulated spectra are shown in FIG. 6 and are similar to the experimental spectra (see FIG. 5). The peak areas with centroids at 1164 keV were calculated and plotted in FIG. 7 (green points and line) and show good agreement between simulated and experimental results.

The observed behavior of the 1164 keV peak area vs NaCl weight percent (w) can be explained as follows. Gamma rays with energy at 1164 keV appear at thermal neutron capture by Cl-35 nuclei. The number of these nuclei ($N_{Cl35}$) in a cubic centimeter of a mixture is:

$$N_{Cl35}(w) = \frac{\rho_{mix}(w) \cdot w \cdot N_{Av} \cdot 0.7578}{Mw} \qquad (1)$$

where:

$$\rho_{mix}(w) = \frac{\rho_{Sand} \cdot \rho_{NaCl}}{\rho_{NaCl} \cdot \left(1 - \frac{w}{100}\right) + \rho_{Sand} \cdot \frac{w}{100}}; \qquad (2)$$

$\rho_{Sand}$, $\rho_{NaCl}$ are the sand and NaCl bulk densities (1.7 g cm$^{-3}$ and 1.15 g cm$^{-3}$, respectively); $N_{Av}=6.02 \cdot 10^{23}$ at mol$^{-1}$ (i.e., Avogadro's number); Mw=58.44 g mol$^{-1}$ is the NaCl molecular weight; and 0.7578 is the Cl-35 abundance. Thermal neutron flux f with depth x changes with a first approximation as:

$$f(x) = f_0 \cdot \exp[-\Sigma_x(w) \cdot x] \qquad (3)$$

where $f_0$ is a thermal neutron flux on the sample surface:

$$\Sigma_x(w) = \sigma_{Cl35} \cdot N_{Cl35}(w) \qquad (4)$$

is a macroscopic cross-section of the thermal neutron interaction; $\sigma_{Cl35}=43.87$ b is a nuclei thermal neutron capture cross section for Cl-35. Note that, due to the relatively high value of this cross-section and high Cl-35 abundance, only the thermal neutron interaction with Cl-35 was taken into account at the first approximation. Gamma flux G can be estimated as:

$$G \sim \int_0^D f_0 \cdot \exp[-\Sigma_x(w) \cdot x] \cdot N_{Cl35}(w) dx = \qquad (5)$$

-continued $$f_0 \cdot \frac{1}{\sigma_{Cl35}} \cdot \{1 - \exp[-\Sigma_x(w) \cdot D]\}$$

The dependence's term $\{1-\exp[-\Sigma_x(w)\cdot D]\}$ with w is plotted in FIG. 7 (blue line) and is very close to experimental values.

Experimental and theoretical calculations demonstrated that dependence of the chlorine TNC signal with chlorine content in mixtures approximately followed the A·[1−exp(−b·w)] curve, where A, b are a constant multipliers. This dependence reaches a saturation level at w more than 40 w %. Since soil contaminated by chlorine is typically much lower, the dependence of the chlorine TNC signal with chlorine content can be approximated by direct proportional dependence with w and can be used as a calibration line for detecting the concentration of chlorine. Thus, our system and method of measurement (in accordance with the present invention) can be used to quantify soil chlorine over a range of concentrations in approximately 30 min.

Signal Value Versus Chloride Surface Density on the Ground

Figure 8:
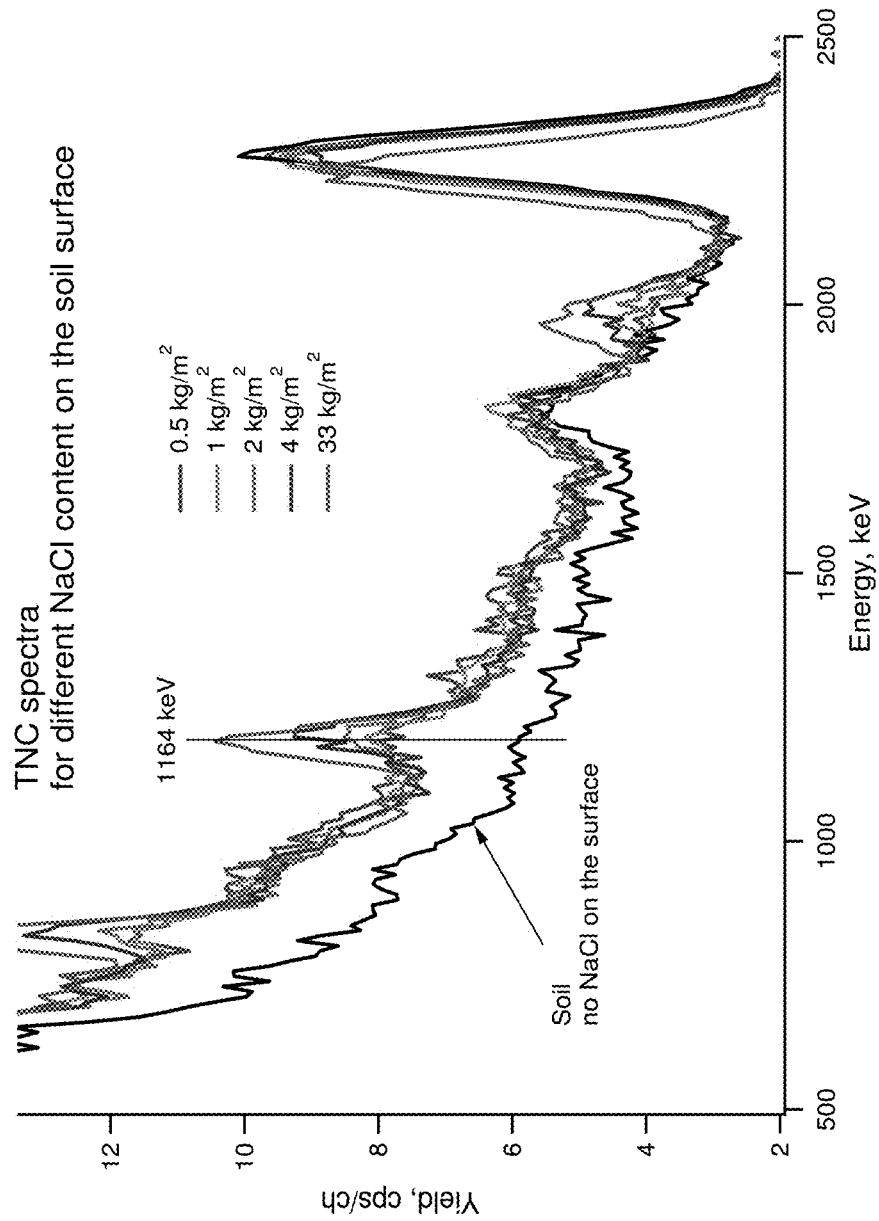
FIG. 8 provides a graph illustrating gamma spectra of soil surfaces contaminated with different amounts of NaCl measured between neutron pulses for a system of the present invention working in pulse mode with a PE moderator.
Figure 9:
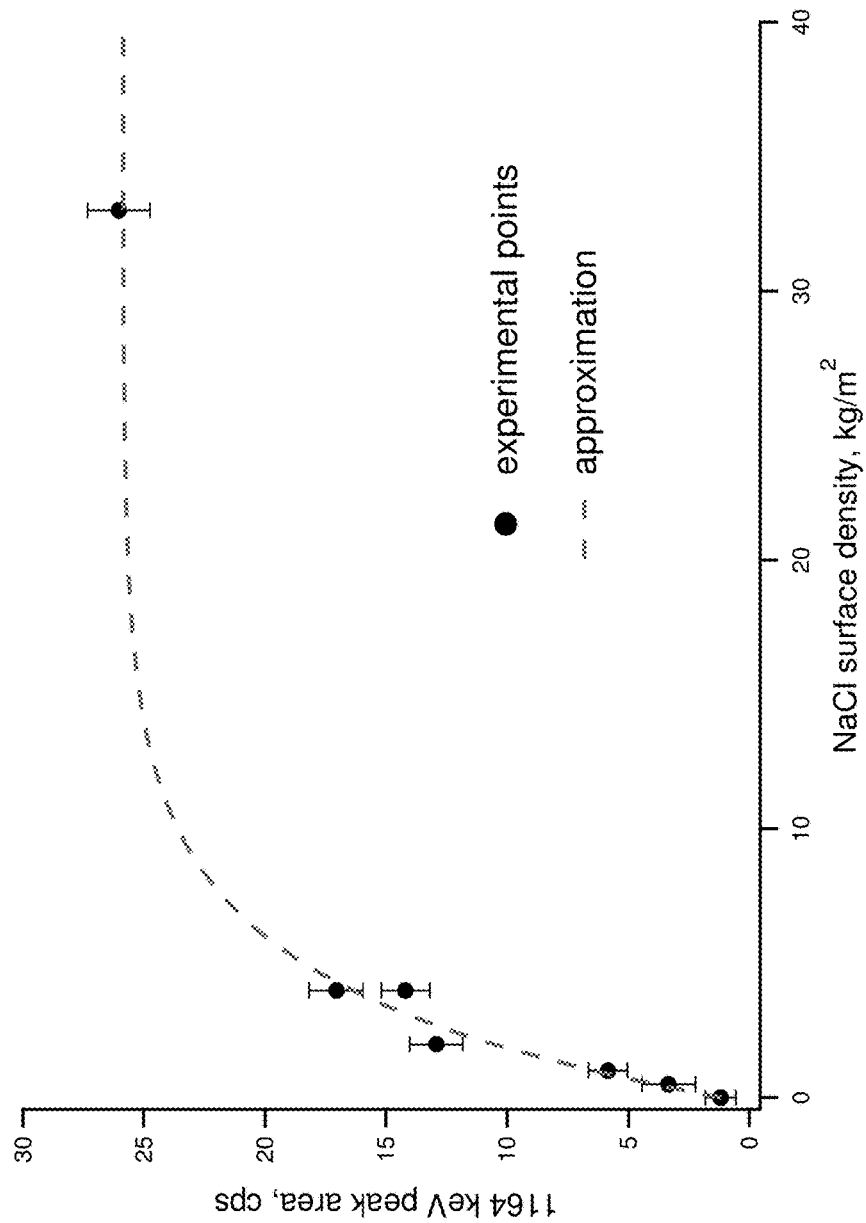
FIG. 9 provides a graph illustrating the dependency of the 1164 keV peak area of the gamma spectra for soil measured between neutron pulses for a system of the present invention working in pulse mode for soil with different moderators vs. NaCl surface density.

Different amounts of sodium chloride were uniformly distributed (manually) in a circular pattern (radius=0.57 m; area=1 m$^2$) to simulate chlorine surface contamination. The mobile system was placed over this area for measurement. Gamma spectra for NaCl surface densities of 0, 0.5, 1, 2, and 4 kg m$^{-2}$ are presented in FIG. 8. The dependence of the peak area with a centroid at 1164 keV versus NaCl surface density is shown in FIG. 9. In addition, FIG. 8 and FIG. 9 include data for a smaller surface area (0.24 m$^2$) with a NaCl surface density of 33 kg m$^{-2}$. As seen in these plots, the peak area with a centroid at 1164 keV increased as NaCl surface density increased and reached saturation at high surface density values. The reason of this behavior (effect of "saturation") was discussed previously (see equation 5). Note that spectrum acquisition time was 3 min. Even with such a short acquisition time, a NaCl content of several hundred grams per m$^2$ on the ground surface can be determined using the system and method of measurement in accordance with the present invention.

Applying the Scanning Regime for NaCl Area Contamination Disclosure

Figure 10:
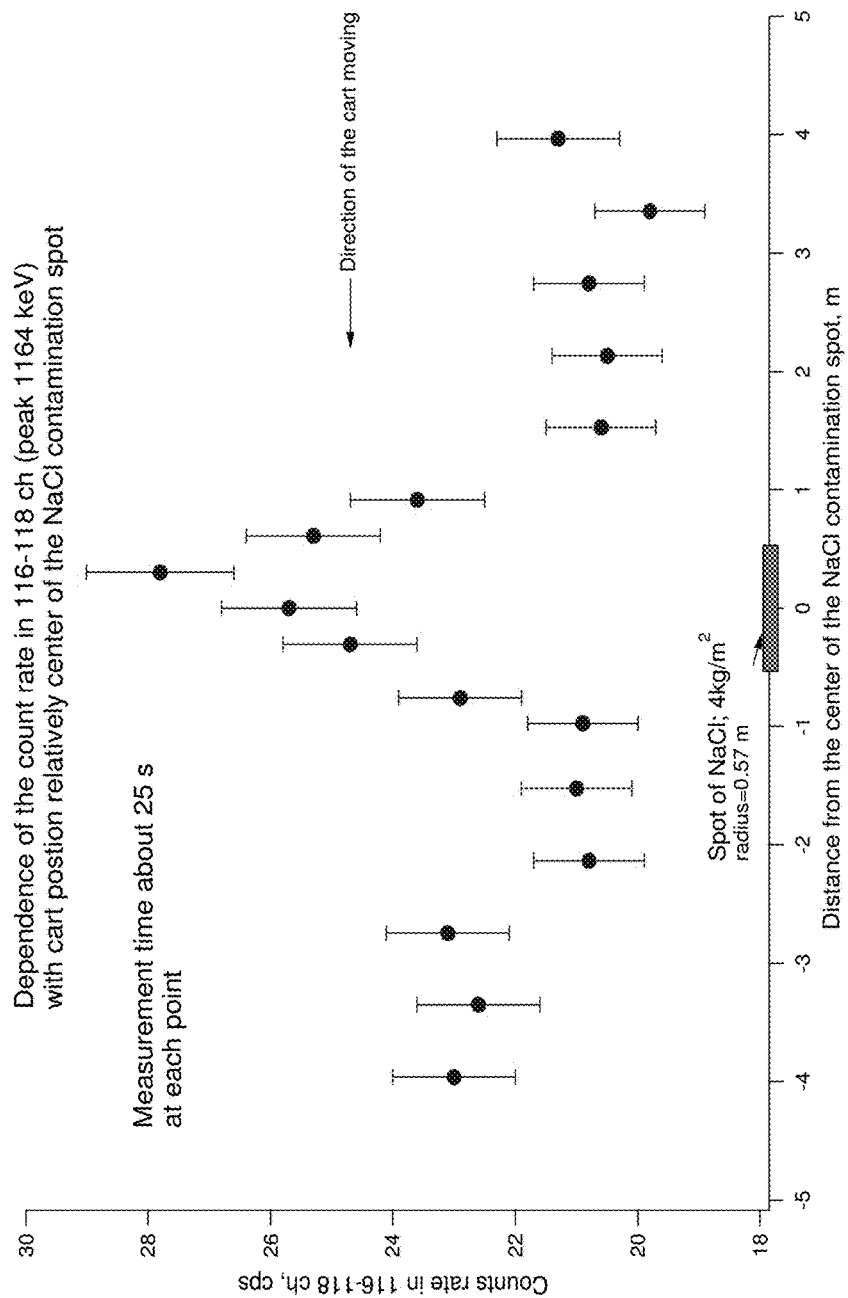
FIG. 10 provides a plot of the count rate around the peak centroid at 1164 keV when a system of the present invention is used to measure chlorine content with different distances relative to the center of an experimental NaCl contamination spot.

Several measurements along a line passing through the center of a 4 kg m$^{-2}$ contamination area were done to model NaCl spot contamination. At each point, 500 counts in three channels around the 1164 keV peak centroid were acquired. Acquisition time was not more than 25 second for each measurement point. From these measurements, count rates and accuracy were determined. The dependence of the count rate in the three channels around peak centroid of 1164 keV is shown in FIG. 10. As can be seen, count rate increased as the mobile system approached the center of the contamination area. Despite the short measurement time at each point (<30 s), areas of chlorine contamination in the field can be located using this system and method of measurement in accordance with the present invention.

Measurements of Objects Containing Chlorine Buried in Soil

Figure 12:
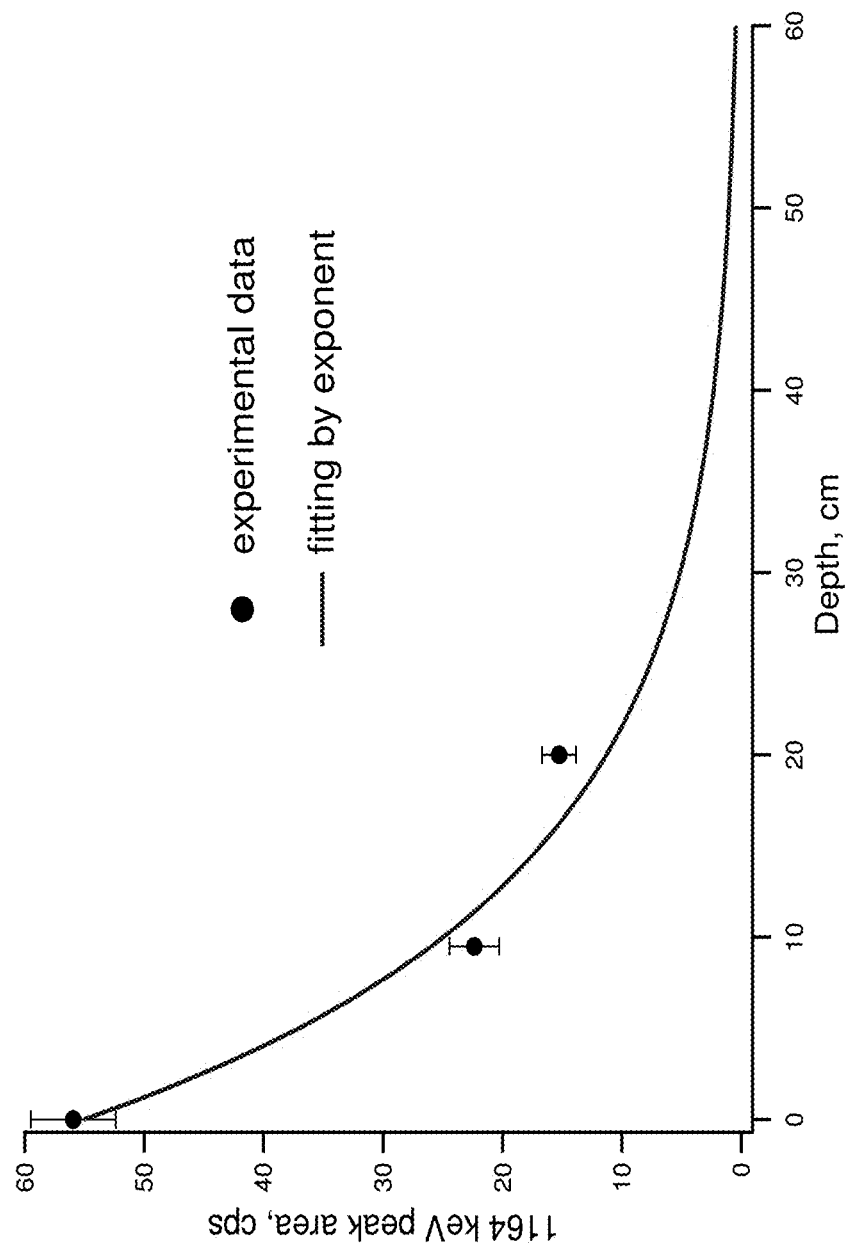
FIG. 12 provides a graph illustrating the dependence of 1164 keV peak area in the gamma spectra of NaCl sample buried at different depths measured between neutron pulses for a system of the present invention working in pulse mode with a PE moderator.

Experiments were conducted to investigate the possibility of using neutron stimulated gamma ray measurements to locate objects containing chlorine that were buried in the soil. A plastic box (34 cm×27 cm×7 cm) containing 6.5 kg NaCl was buried at different soil depths. Thermal neutron stimulated gamma spectra were measured for each depth. Each measurement continued for 5-7 minutes. Measurement results (gamma spectra) are presented in FIG. 11. As can be seen, the peak with a centroid at 1164 keV decreased as depth increased. Note that the value of this spectra peak is large enough to locate an object buried to 20 cm, possibly deeper. The exponential decrease of this peak with depth is shown in FIG. 12. From the present results, we conclude that the system and method of measurement in accordance with the present invention has the potential to locate an object containing several kilograms of chlorine to a depth of several dozen centimeters beneath the soil surface.

Nitrogen Detection System

Using fast neutrons (14 MeV) can be utilized for detection nitrogen (2.31 and 5.11 MeV), as well as other elements, for instance, C (4.43 MeV), O (6.13 MeV), Al (2.21 and 2.98 MeV), and Fe (1.24, 1.81, and 2.60 MeV) [Valkovic, 2016]. But inelastic scattering cross-sections of the fast neutrons with Nitrogen (N) for producing major gamma lines at 2.31, 4.46 and 5.1 MeV is lower (by about a factor of three) than the cross-sections production of the major lines at 4.43 and 6.13 MeV for C and O, respectively. The results is a very weak signal which is not observable above the high background from surrounding material [Mitra, 2012]. This precludes using this reaction for N detection when work with conventional micro-second pulsed 14 MeV neutron generator as described by Mitra (2012). On the other hand, the thermal neutrons capture reaction can be used for nitrogen determination, and the prompt gamma line with energy of 10.83 MeV which appears due to thermal neutron capture by nitrogen is suitable for this purpose [Uhm, 1995; Panjeh, 2011; Chichester, 2004].

Some specialized equipment used for soil carbon content determination can carry out measurements of the neutron gamma stimulated spectra due to inelastic neutron scattering (INS) and thermal neutron capture (TNC) separately. The special adjustment of electronic system gamma registration parameters can prolong the energy range of spectra registration till 12 MeV (instead of 8 MeV). Currently, the 14 MeV neutron flux is used for carbon registration. The application polyethylene sheets with a thickness around 5 cm as a moderator will effectively convert high energy neutron flux to thermal neutron flux that is needed for the stimulating of TNC reactions on nitrogen. Also, because of the split electronics present in the specialized equipment, INS and TNC spectra can be measured simultaneously. So, without polyethylene moderator it is possible to measure C and N signal at the same time, providing the possibility to determine the C/N ratio in samples.

Materials for Testing

Nitrogen containing materials were chosen for experiments to determine the possibility of using the available equipment for the application for nitrogen determination. The materials chosen were: ammonium sulfate, ammonium nitrate, urea, and melamine. The chemical formula, nitrogen weight percent, density and bulk density, and other characteristics of these substances are given in Table 4. Note, bulk densities of the listed substances were determined by measurements.

TABLE 4

Characteristics of nitrogen containing substances

| Material | Formula, molar mass, g/mol | Nitrogen w % | Bulk density, (density) g/cm$^3$ | N14 nuclei # per cm$^3$ | $\Sigma_x$, cm$^{-1}$ | $\mu$, cm$^{-1}$ at 10.8 MeV |
|---|---|---|---|---|---|---|
| Ammonium | (NH$_4$)$_2$SO$_4$ 132.14 | 21 | 1.175 (1.77) | 1.07E22 | 0.018 | 0.027 |

TABLE 4-continued

Characteristics of nitrogen containing substances

| Material | Formula, molar mass, g/mol | Nitrogen w % | Bulk density, (density) g/cm³ | N14 nuclei # per cm³ | $\Sigma_x$, cm⁻¹ | µ, cm⁻¹ at 10.8 MeV |
|---|---|---|---|---|---|---|
| sulfate | | | | | | |
| Ammonium Nitrate | NH₄NO₃ 80.052 | 34 | 1.009 (1.73) | 1.52E22 | 0.011 | 0.021 |
| Urea | (NH₂)₂CO 60.06 | 46 | 0.778 (1.32) | 1.56E22 | 0.012 | 0.016 |
| Melamine | C₃H₆N₆ 126.12 | 67 | 0.926 (1.57) | 2.66E22 | 0.011 | 0.019 |

Modelling Calculation of Nitrogen Gamma Response and Estimation of Samples Parameters for Measurements.

Estimates of the required sample parameters (sizes, nitrogen content in samples) for modelling the calculation of dependencies of gamma response versus sample thickness were done for substances with different nitrogen content. The gamma response intensity for nitrogen containing materials can be estimated based on a gamma response model [Yakubova, 2014]. Based on this model, the gamma respond intensity $N_y$ from a slab of material with thickness H can be estimated as:

$$N_\gamma(H) \sim \sigma_N N_{NperCC} \times$$

$$\int_{-\infty}^{\infty} \int_0^{H/\sin\varphi} \int_0^\pi \frac{\exp\{-\Sigma_x \cdot [r^2 + (z+a)^2]^{\frac{1}{2}}\} \cdot r^2 \cdot \sin(\varphi)}{(r^2 + z^2)^{3/2} \cdot [r^2 + (z+a)^2]} \left(\exp\left[-\mu \cdot (r^2 + z^2)^{\frac{1}{2}}\right]\right) dz dr d\varphi$$

where $\sigma_N$ is a thermal neutron capture cross-section by nitrogen nuclei, $N_{NperCC}$ is a number of nitrogen nuclei per cubic centimeter, a is the distance between the source and the detector, $\Sigma_x$ is a linear macroscopic cross-section of neutron interaction with material, and µ is the mass-attenuation coefficient of gamma rays with energy of 10.8 MeV in the material.

$N_{NperCC}$ can be calculated by equation:

$$N_{NperCC} = \frac{\rho \cdot A_{Av}}{Mw} \cdot n_N$$

where ρ is the material bulk density, $A_{Av}$ is the Avogadro number, Mw is a molecular weight, $n_N$ is a number of nitrogen nuclei in molecule. Calculated values of nitrogen nuclei number per cubic centimeter of the listed materials are presented in Table 4 as well.

$\Sigma_x$ can be calculated as:

$$\Sigma_x = \frac{\rho \cdot A_{Av}}{Mw} \sum n_i \cdot \sigma_i$$

where $n_1$—the number of the nuclei of i-th element in molecule, a is a thermal neutron cross-section for i-th element.

µ can be calculated as:

$$\mu = \rho \cdot \sum \mu_i \cdot \frac{Aw_i \cdot n_i}{Mw}$$

where $\mu_i$ is the mass-attenuation coefficient of gamma rays with energy 10.8 MeV for i-th element in molecule, and $Aw_i$ is the atomic weight of this element. The values of $\sigma_i$ and $\mu_i$ for nuclei in tested substances are given in Table 5 [IAEA, 2014; NIST 2015], and calculated values of $\Sigma_x$ and µ are given in Table 4.

TABLE 5

Thermal neutron capture cross-section of nuclei and mass attenuation coefficient of elements in tested substances [IAEA, 2014; NIST 2015].

| Element | Thermal neutron capture cross-section, barn | Mass attenuation coefficient of 10.8 MeV gamma rays, cm²/g |
|---|---|---|
| O | 0.00019 | 0.0208 |
| N | 0.0795 | 0.0202 |
| H | 0.3326 | 0.0325 |
| C | 0.0035 | 0.0195 |
| S | 0.53 | 0.0259 |

Figure 13:
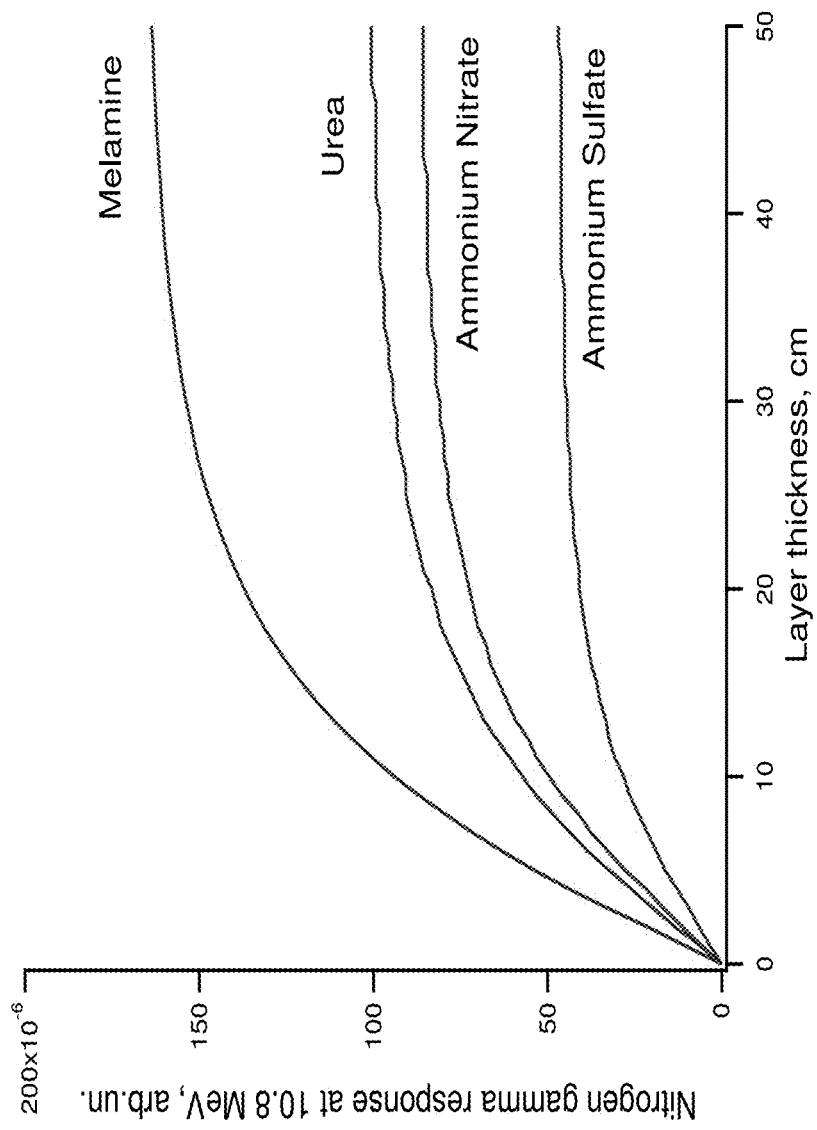
FIG. 13 shows dependencies of nitrogen gamma response from thermal neutron irradiated ammonium sulfate, ammonium nitrate, urea and melamine with slab thickness.

The dependencies of the nitrogen gamma response (for gamma line at 10.8 MeV) for ammonium sulfate, ammonium nitrate, urea, and melamine from thermal neutron irradiation with slab thicknesses were calculated and are presented in FIG. 13. As can be seen, these dependencies reach the practical level of saturation at the slab thickness of 50 cm. Note: the gamma flux from a slab with a thickness of 20 cm is equal to approximately 83-87% of the level of saturation in all cases (this sample thickness was used in the experiments).

Figure 14:
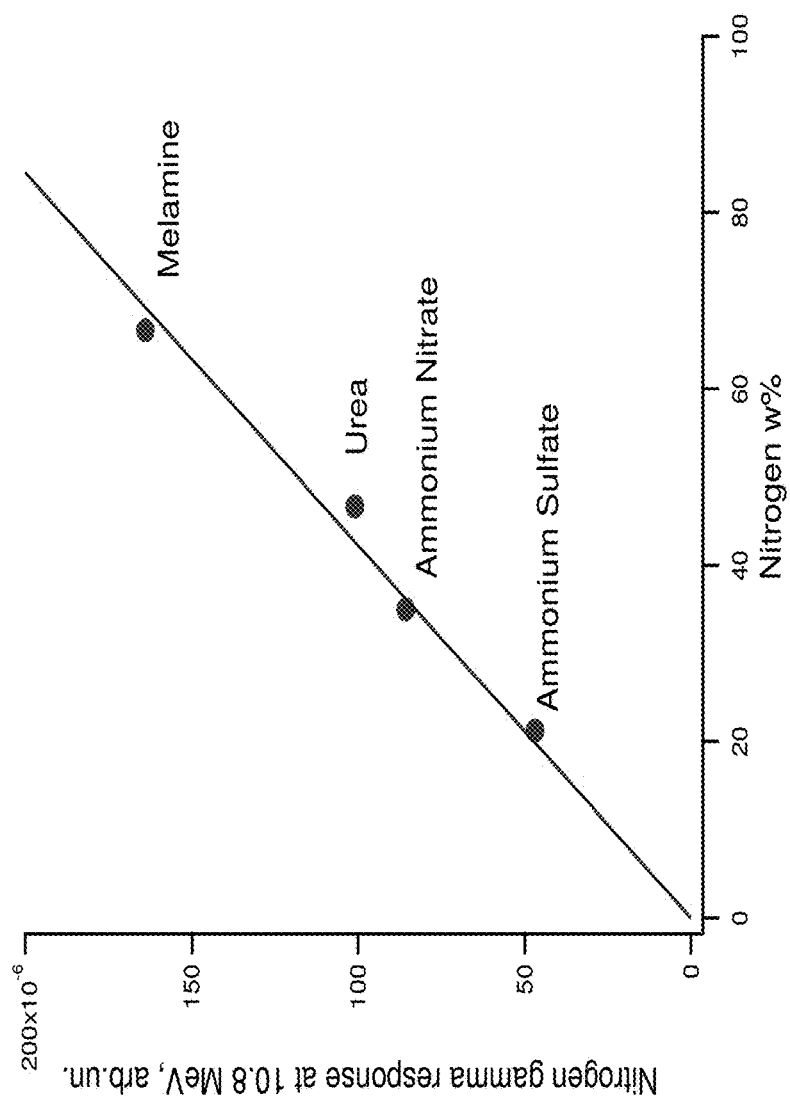
FIG. 14 shows dependence of nitrogen gamma response from thermal neutron substances with nitrogen weight percent.

The dependence of gamma flux saturation level from slab versus nitrogen weight percentage in substances are shown in FIG. 14. As expected, the nitrogen gamma response from 20 cm thickness slab increases in direct proportion to nitrogen content in the substances. (Note: such dependence for chlorine reaches the level of saturation at ~30% chlorine content in a 20 cm slab due to a much higher value of thermal neutron capture cross-section with this element.) Thus, for the experimental study of the nitrogen gamma response from nitrogen containing materials under thermal neutron irradiation, samples should have a slab thickness of at least 20 cm (length and wide more) and with nitrogen content of more than several dozen weight percentage.

Monte-Carlo Simulation of Neutron Stimulated Gamma Spectra from Nitrogen Containing Substances.

Information regarding the shape of the gamma spectra of nitrogen containing materials from thermal neutron irradiation was determined using Monte-Carlo (MC) simulation with Geant4.10.01.p01 tools kit. The simulation model was quite similar to experimentally collected data. Nitrogen containing samples (60×60×20 cm³) were placed on sand substrate (150×150×60 cm³). The simulation included the following components. A neutron source was 10 cm above the upper sample surface. Sodium Iodate detector with radial cross-section 12.7×15 cm² and inner diameter 55 cm surrounded the neutron source. The shielding from borated polyethylene and lead was situated between the source and the detector to protect the detector from the direct neutron flux. The polyethylene moderator was placed underneath the source (between the source and the sample) to convert fast 14.1 MeV neutron flux to thermal neuron flux.

Figure 15:
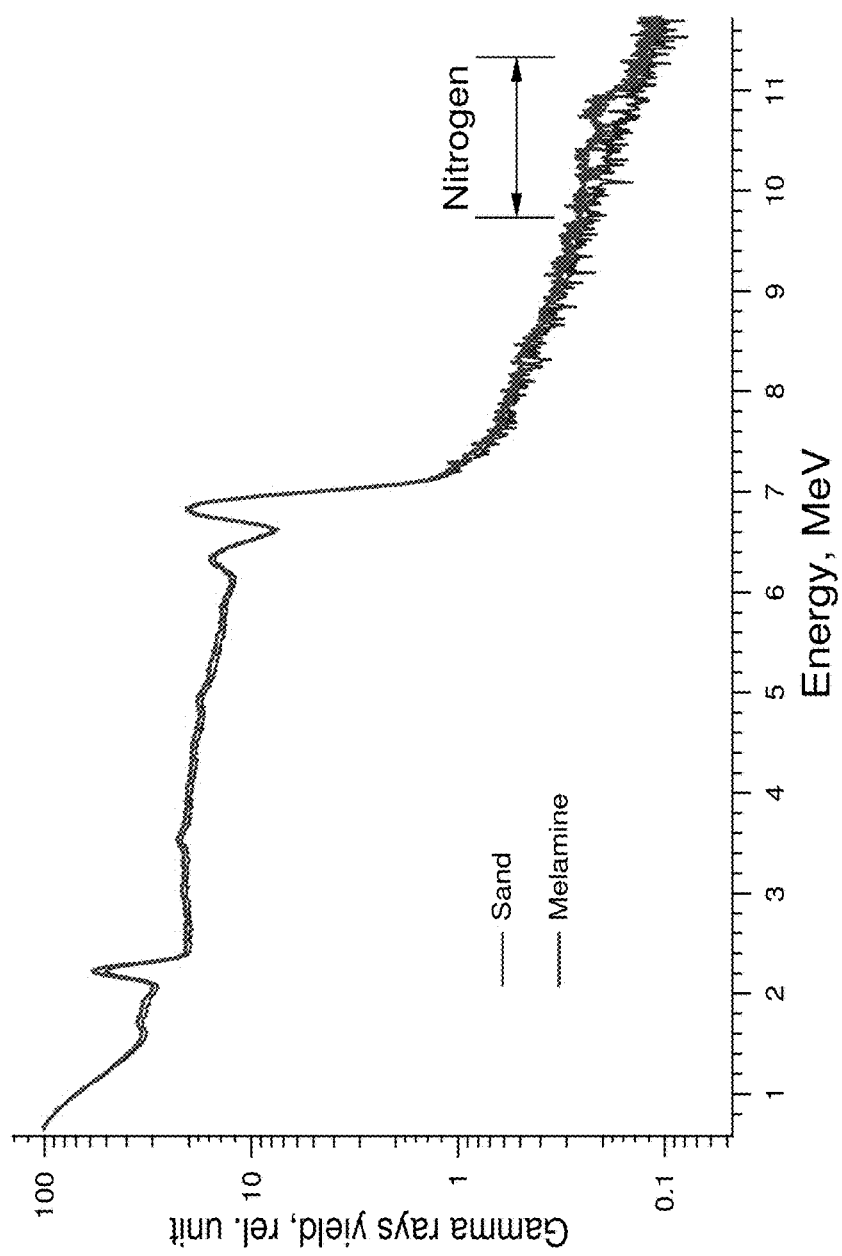
FIG. 15 shows Geant4 simulated gamma spectra of sand substrate (blue) and melamine on sand substrate (red) at neutron irradiation.
Figure 16:
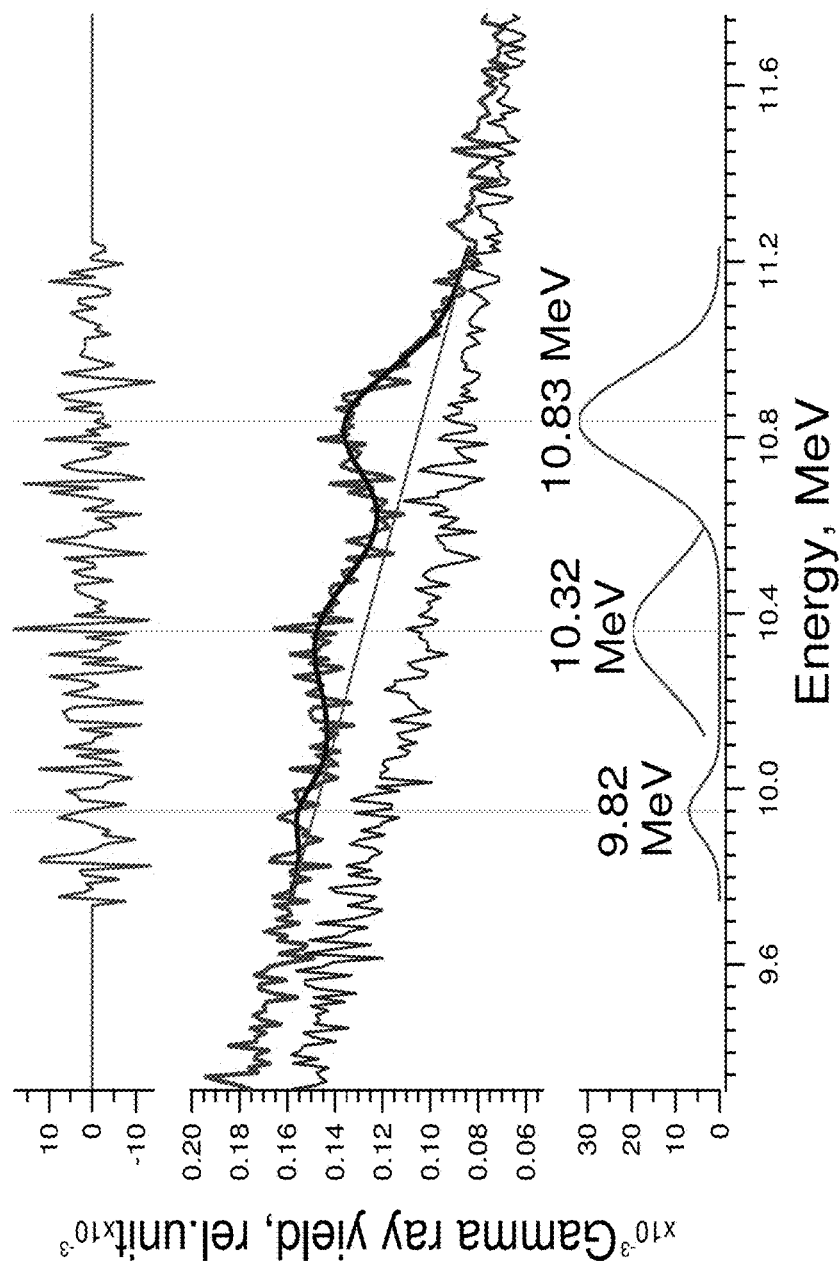
FIG. 16 shows Nitrogen peaks and its approximation by three Gaussians.

Results of the spectra simulation for a melamine sample and for the spectra without a sample (irradiated material was only a sand substrate) are shown in FIG. 15. As can be seen, the nitrogen peak in the spectra had a centroid at 10.83 MeV. This position agrees with reference data [NNDC, 2013]. The neighboring peaks have centroids at 10.32 MeV and at 9.82 MeV and can be identified as a single escape peak (difference 10.83-10.3≈0.511 MeV) and double escape peak (difference 10.83-9.82≈1.022 MeV). Because of the low value of nitrogen thermal neutron capture cross-section, the nitrogen peaks intensity is low. Simulation of the 2·10⁹ neutrons propagation was accumulated to provide the spectra with noise shown in figures. The time required for this simulation would be equal to several hundred hours, even in multi-thread mode on high performance cluster computer.

Figure 17:
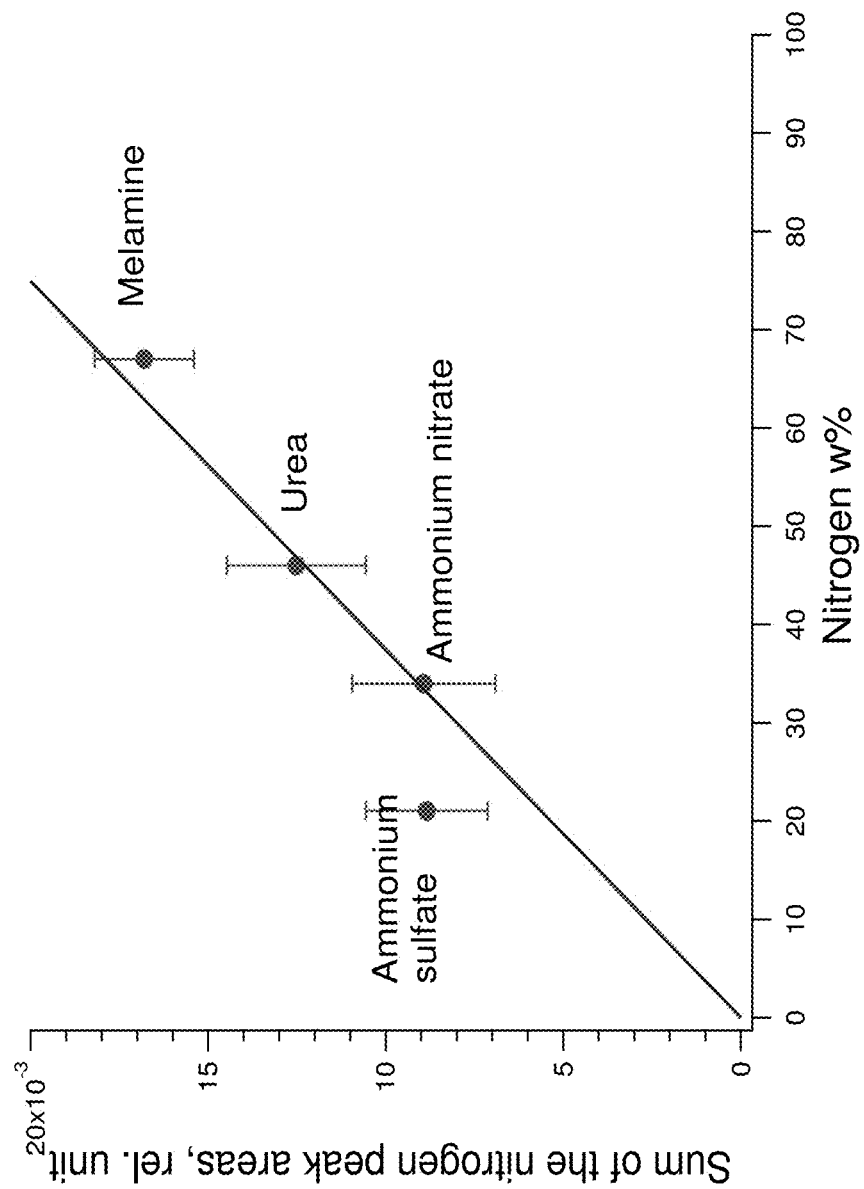
FIG. 17 shows Monte-Carlo simulated dependence of nitrogen gamma peak areas in 10.8 MeV range with nitrogen weight percent.

The dependence of total peak areas in nitrogen energy range with nitrogen weight percentage for ammonium sulfate, ammonium nitrate, urea, and melamine was calculated and is represented in FIG. 17. This dependence can be approximated with a line. Thus, the results of MC simulation for condition of our experimental setup confirm the possibility of the nitrogen determination in nitrogen containing materials. However, because of the high noise level, large errors occur in the peak area calculations resulting in the material with the lowest nitrogen content falling off the approximation line.

Figure 18:
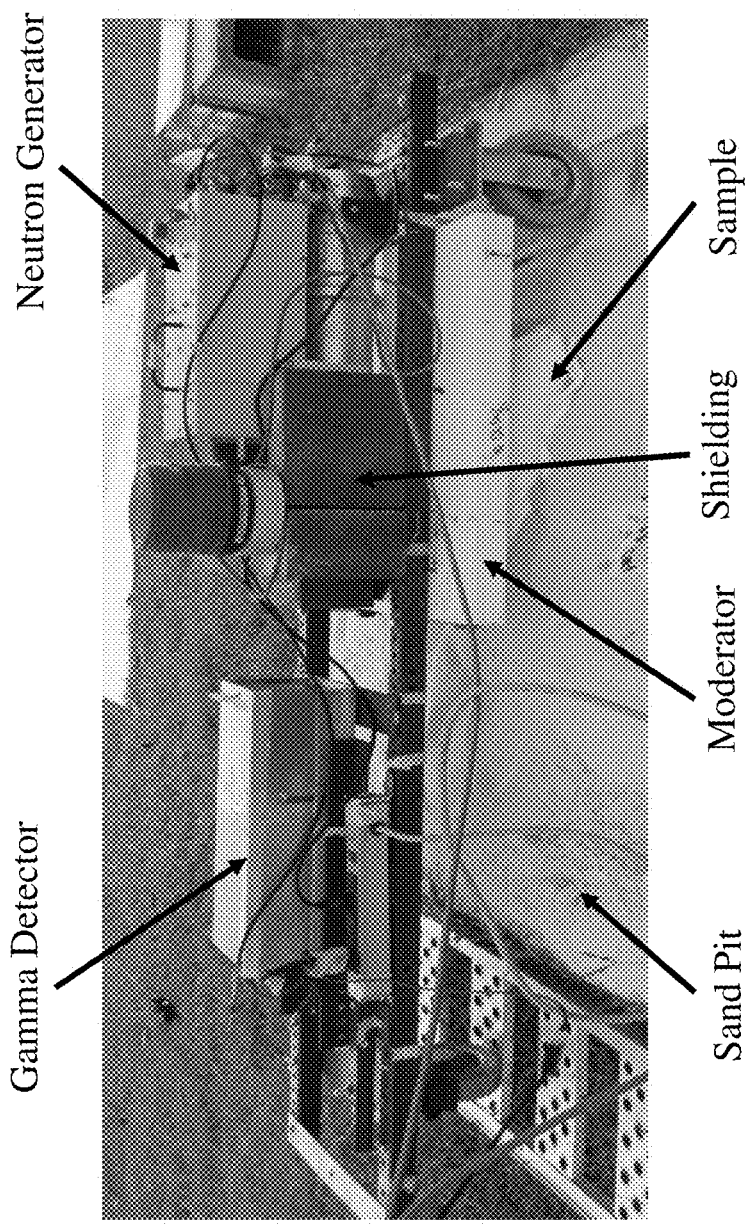
FIG. 18 shows experimental setup for measurements of the neutron stimulated spectra (similar to the configuration shown in FIGS. 1.A, 1.B, and 2.
Figure 19:
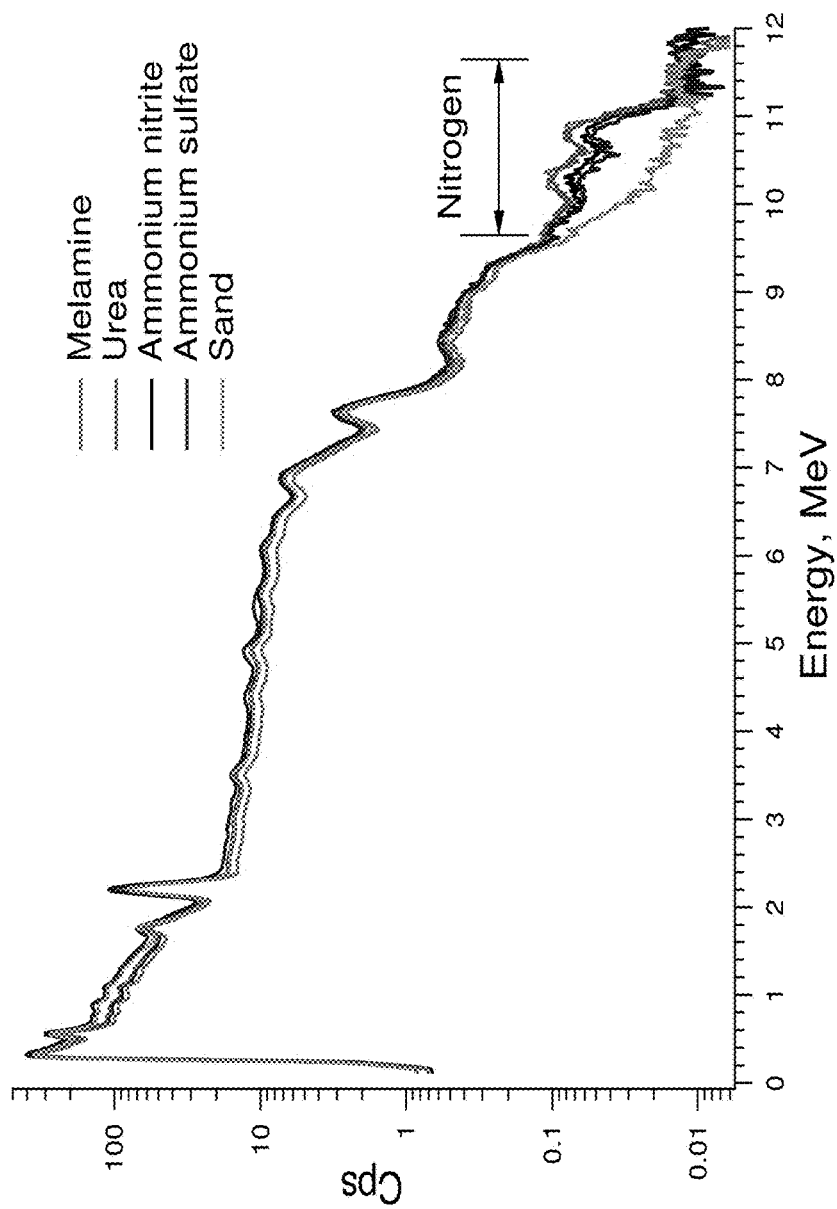
FIG. 19 shows thermal neutron stimulated gamma spectra for ammonium sulfate, ammonium nitrate, urea, and melamine.
Figure 20:
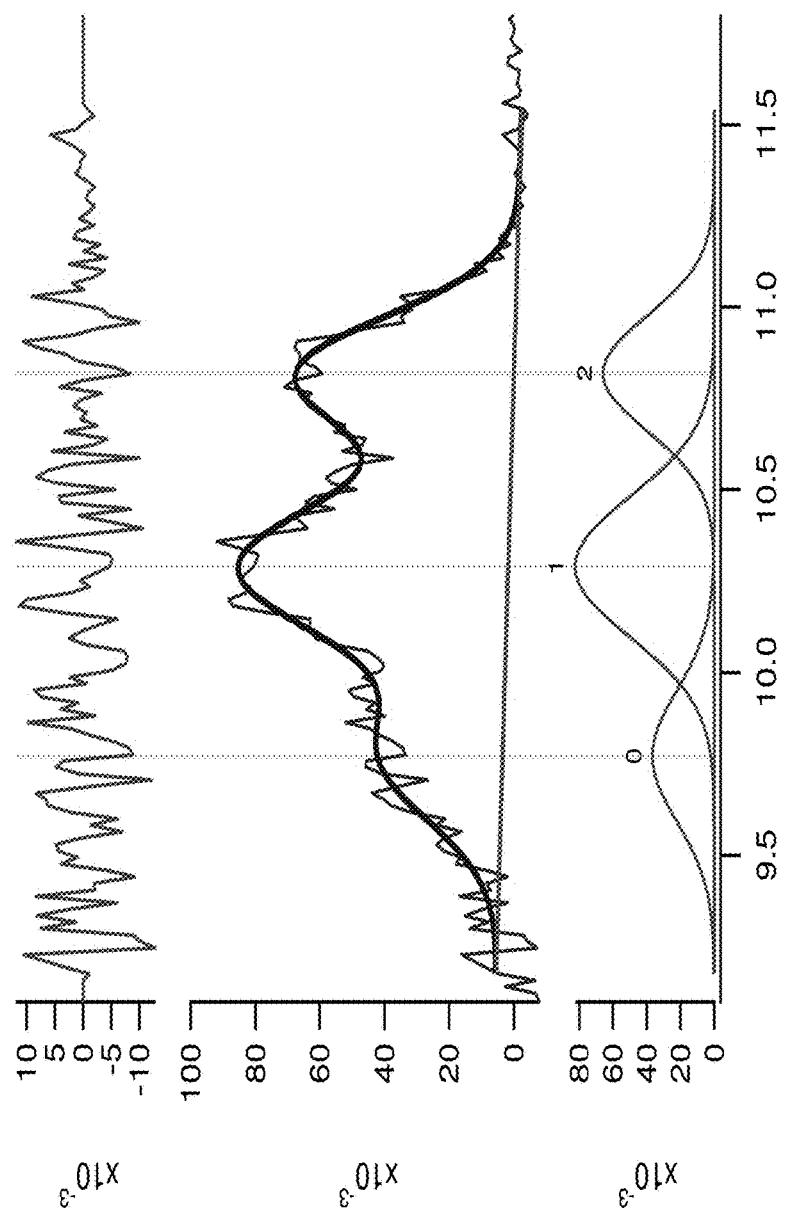
FIG. 20 shows neutron stimulated net TNC gamma spectra of Melamine in 9.2-11 MeV energy range, and their fitting by three Gaussian peaks.
Figure 21:
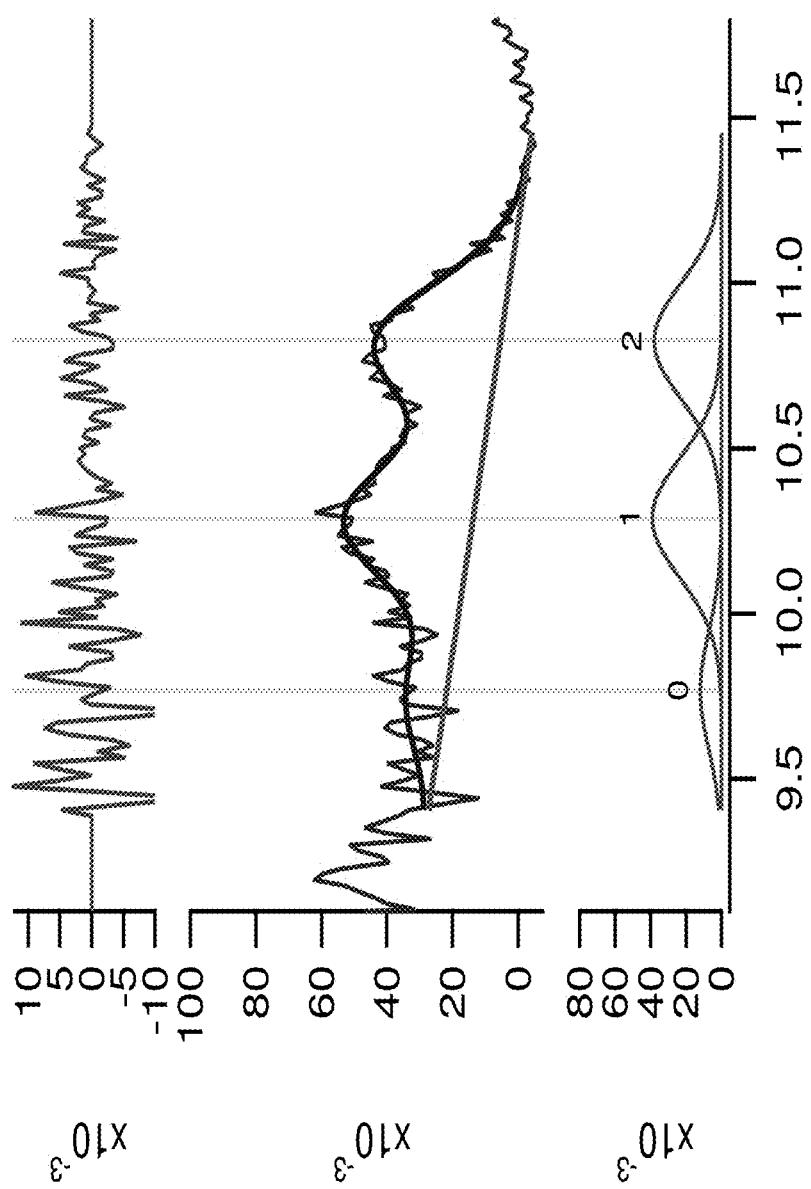
FIG. 21 shows neutron stimulated net TNC gamma spectra of Ammonium nitrate in 9.2-11 MeV energy range, and their fitting by three Gaussian peaks.
Figure 22:
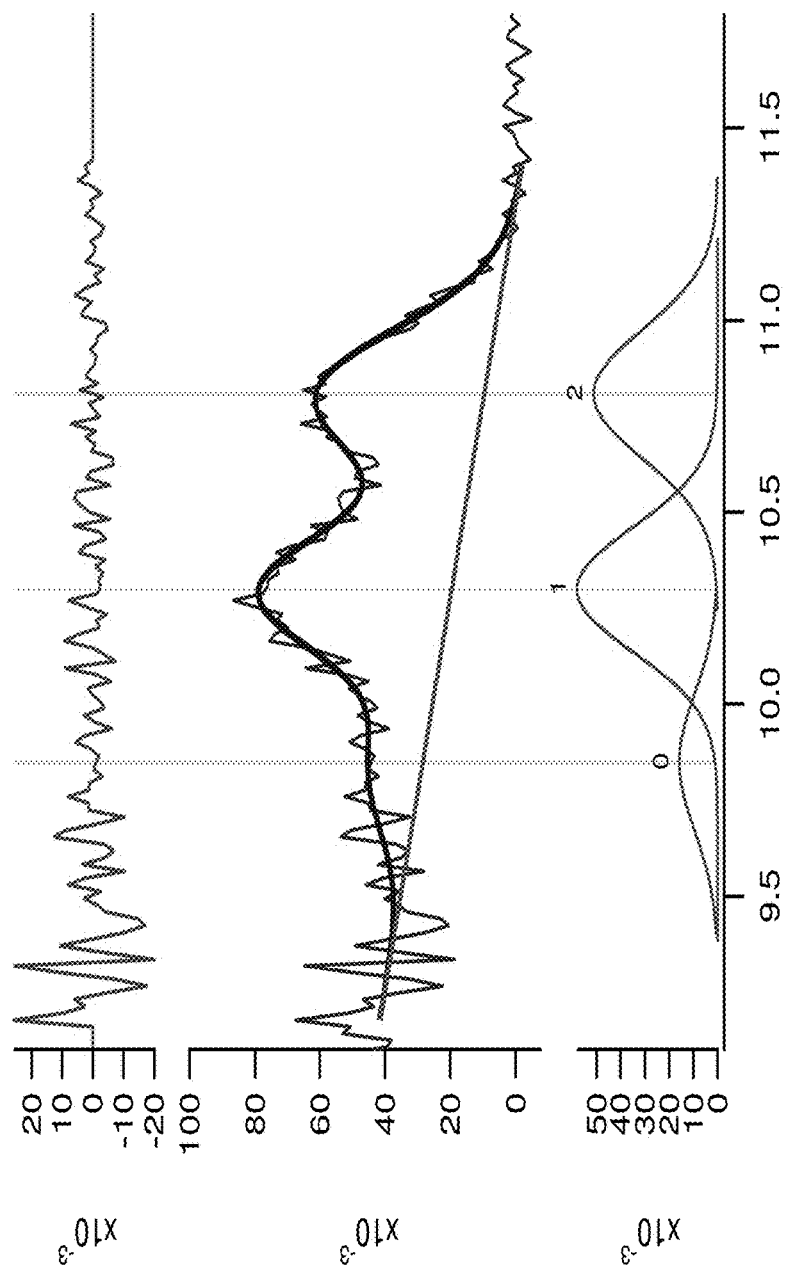
FIG. 22 shows neutron stimulated net TNC gamma spectra of Urea in 9.2-11 MeV energy range, and their fitting by three Gaussian peaks.
Figure 23:
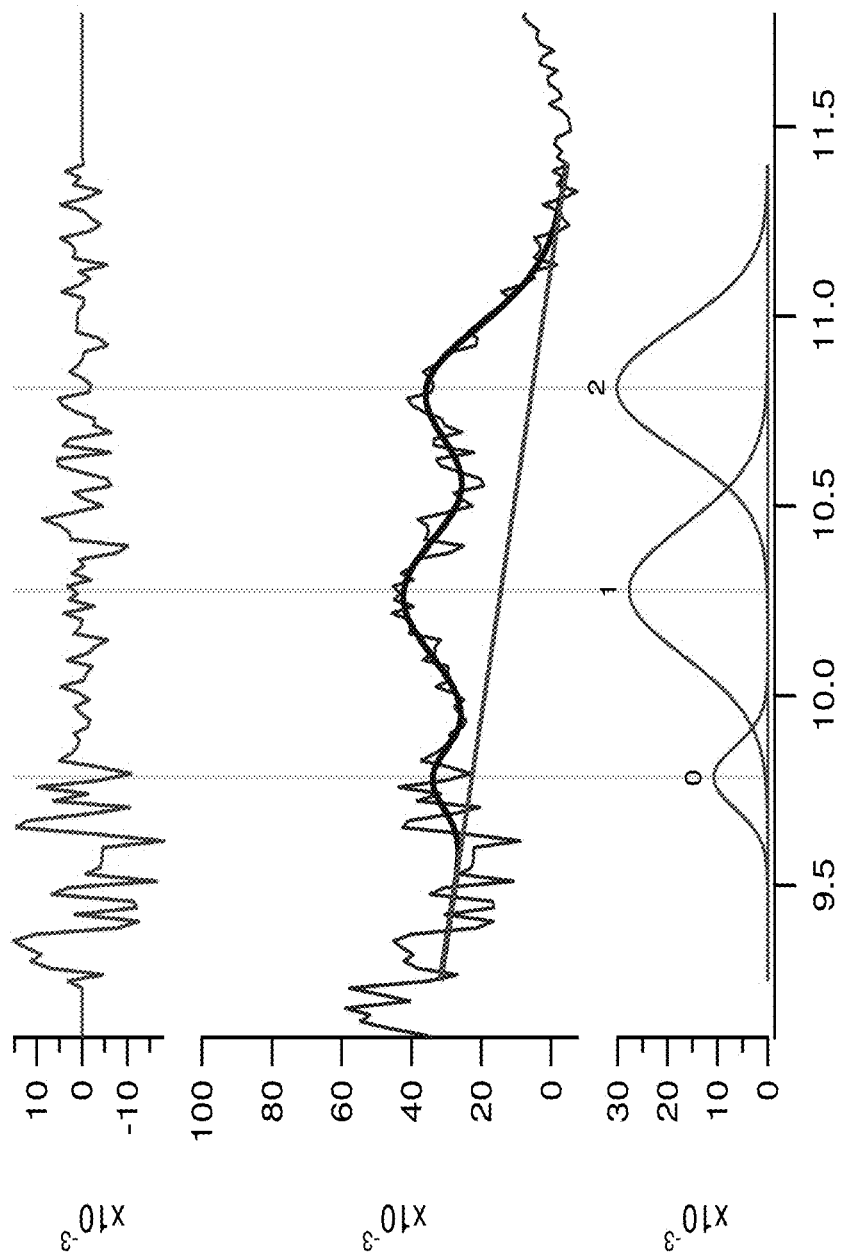
FIG. 23 shows neutron stimulated net TNC gamma spectra of Ammonium sulfate in 9.2-11 MeV energy range, and their fitting by three Gaussian peaks.

Measurements of Neutron Stimulated Gamma Spectra of Nitrogen Containing Substances Measurements of neutron stimulated gamma spectra from ammonium sulfate, ammonium nitrate, urea, and melamine were conducted with the equipment setup shown in FIG. 18. This setup consists of a neutron generator, a gamma detector and polyethylene moderator to convert high energy (14.1 MeV) neutron flux to thermal neutron flux. The borated polyethylene with lead and lead shielding were used, and serve to protection of the gamma detector from direct neutron flux and as a biological shielding. Samples of nitrogen containing substances with weight near 22.7 kg (50 lb) and size dimensions of 60×40×20 cm³ were placed on a dry sand substrate (150×150×60 cm³) for these measurements. The acquired spectra for the above listed substances are shown in FIG. 19.

The presence of nitrogen in substances resulted in several peaks in the high energy region (9.5-11 MeV). A procedure to calculate the total area of these peaks was used. The sand spectrum was subtracted from each spectra, channel by channel, to provide a net gamma spectra. Spectra in the range from 9.2-11.6 MeV which were returned as a result of this operation were fitted by three Gaussian peaks. As can be seen in FIGS. 20-23, there was a good fit agreement with the measured spectra indicating that so this fitting data can be used for analysis. The peak positions and total peak areas for each spectra are represented in Table 6.

TABLE 6

Peak positions and total peak areas in nitrogen energy range of neutron stimulated gamma spectra for ammonium sulfate, ammonium nitrate, urea, and melamine.

| Substance | Peak positions ± error, MeV | | | Δ Peak positions ± error, MeV | | Total peak area ± error, arb.un. |
|---|---|---|---|---|---|---|
| | 2 | 1 | 0 | 2 − 1 | 2 − 0 | |
| Melamine | 10.819 ± 0.009 | 10.290 ± 0.009 | 9.772 ± 0.023 | 0.529 ± 0.013 | 1.047 ± 0.025 | 0.074 ± 0.004 |
| Ammonium nitrate | 10.824 ± 0.001 | 10.289 ± 0.012 | 9.767 ± 0.046 | 0.535 ± 0.017 | 1.057 ± 0.048 | 0.039 ± 0.003 |
| Urea | 10.808 ± 0.001 | 10.299 ± 0.012 | 9.848 ± 0.044 | 0.509 ± 0.016 | 0.960 ± 0.046 | 0.052 ± 0.003 |
| Ammonium sulfate | 10.811 ± 0.002 | 10.277 ± 0.017 | 9.785 ± 0.023 | 0.534 ± 0.017 | 1.026 ± 0.028 | 0.026 ± 0.002 |

Figure 24:
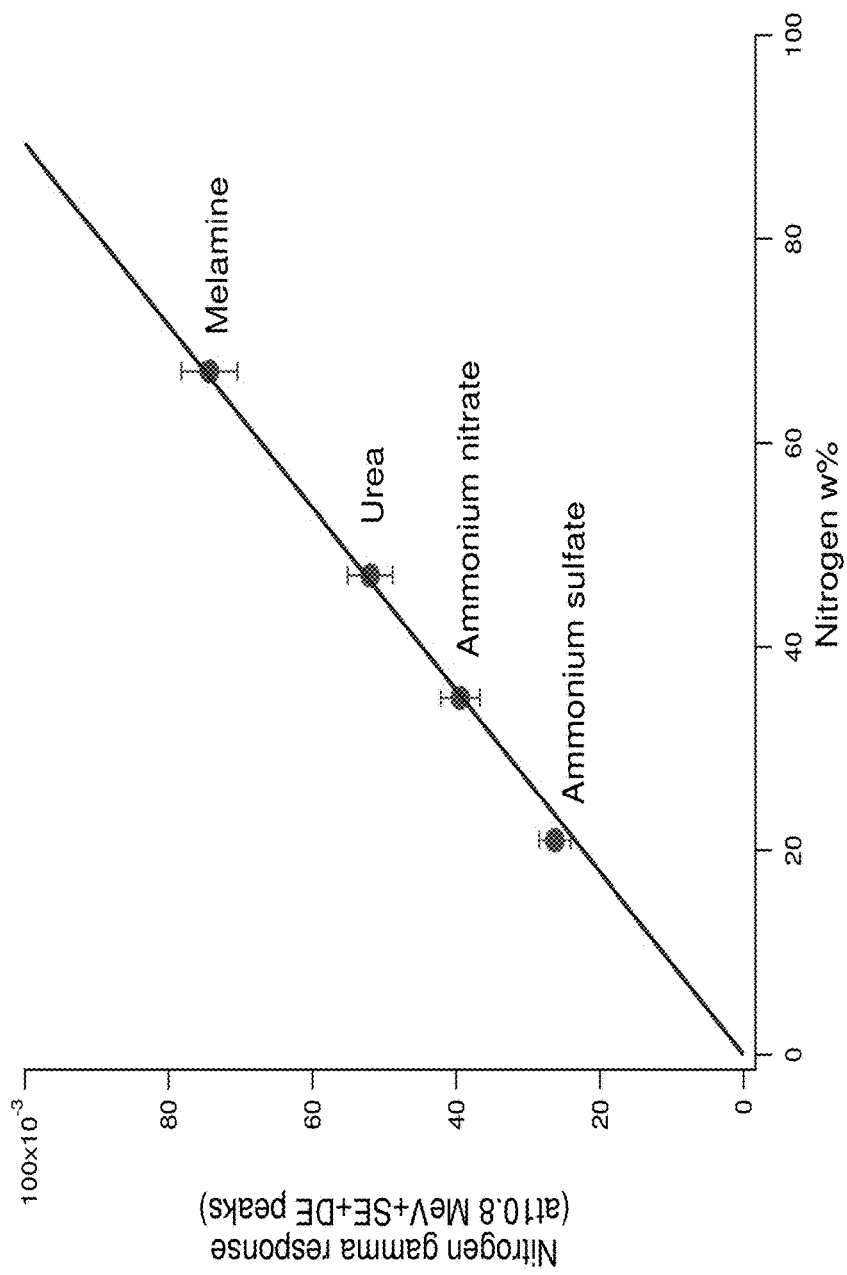
FIG. 24 shows nitrogen gamma response versus nitrogen weight percent.

The data from Table 6 was used developing the next conclusions regarding the nature of the peaks in the range of 9.2-11.6 MeV, which can be termed "nitrogen range". The position of the peak 2 for all substances agrees in the limit of the experimental error with position of nitrogen neutron capture prompt gamma line and, so, can be attributed to this process. The shifts between peaks 1 and 0 relative to the position of peak 2 can be estimated as 0.511 MeV and 1.022 MeV within the limit of the experimental error. Therefore, peak 1 can be attributed to a single escape (SE) peak and peak 2 to a double escape (DE) peak of 10.8 MeV gamma peak. So, these three peaks all together can be associated with the total amount of nitrogen in the sample. The dependence of total peaks area in "nitrogen range" versus nitrogen weight percentage of substances are represented in FIG. 24. As was predicted by the gamma response calculations by the Yakubova (2014) model (see FIG. 14), the measured dependence of the gamma response to nitrogen weight percentage was directly proportional.

Measurements of the Nitrogen Signal from Melamine Sample Buried into the Sand

Figure 25:
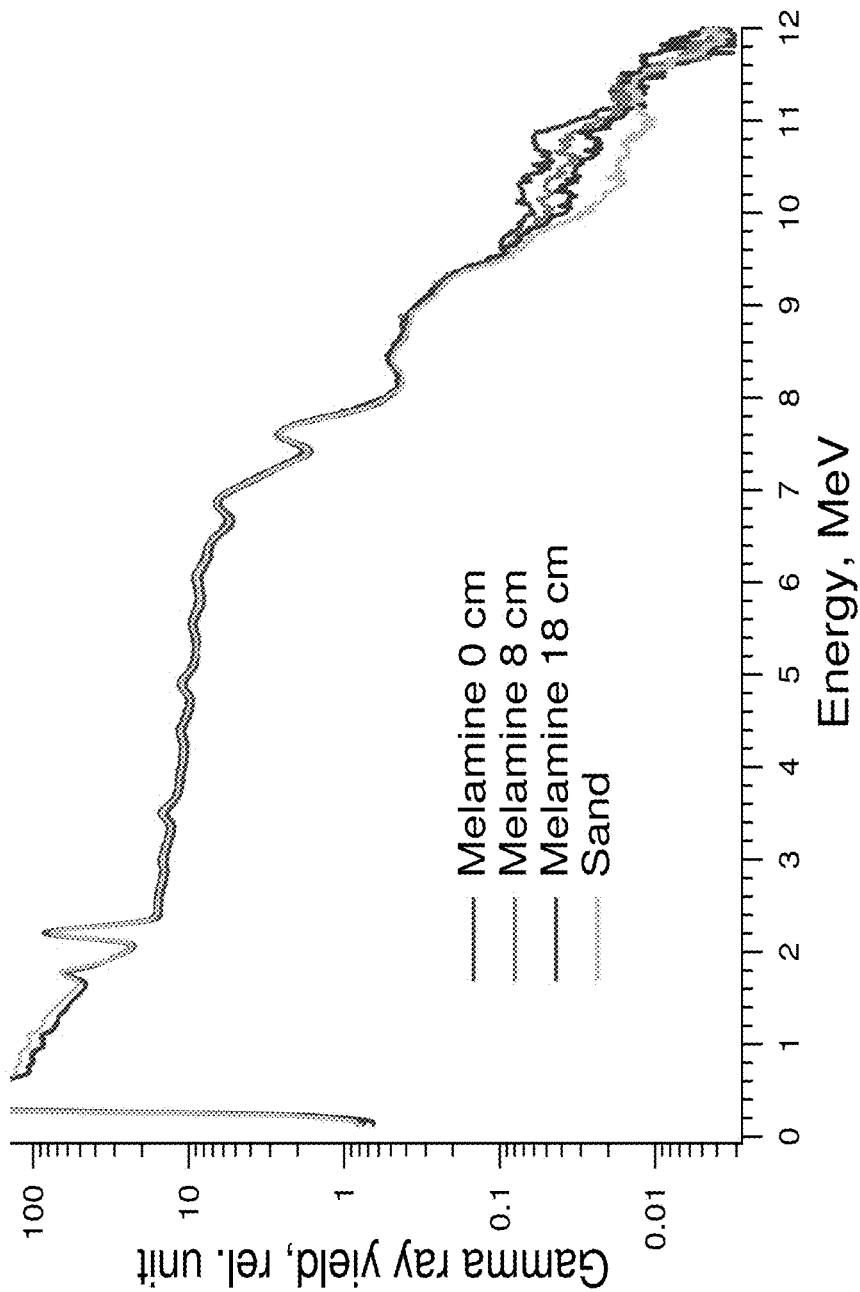
FIG. 25 shows neutron stimulated gamma spectra from 25 kg melamine sample buried on different depth into the sand.

To estimate the possibility of using the current modified measurement system to detect buried nitrogen containing substance, the spectra from 25 kg melamine sample buried at different depths were acquired. Results of these measurements are shown in FIG. 25.

Figure 26:
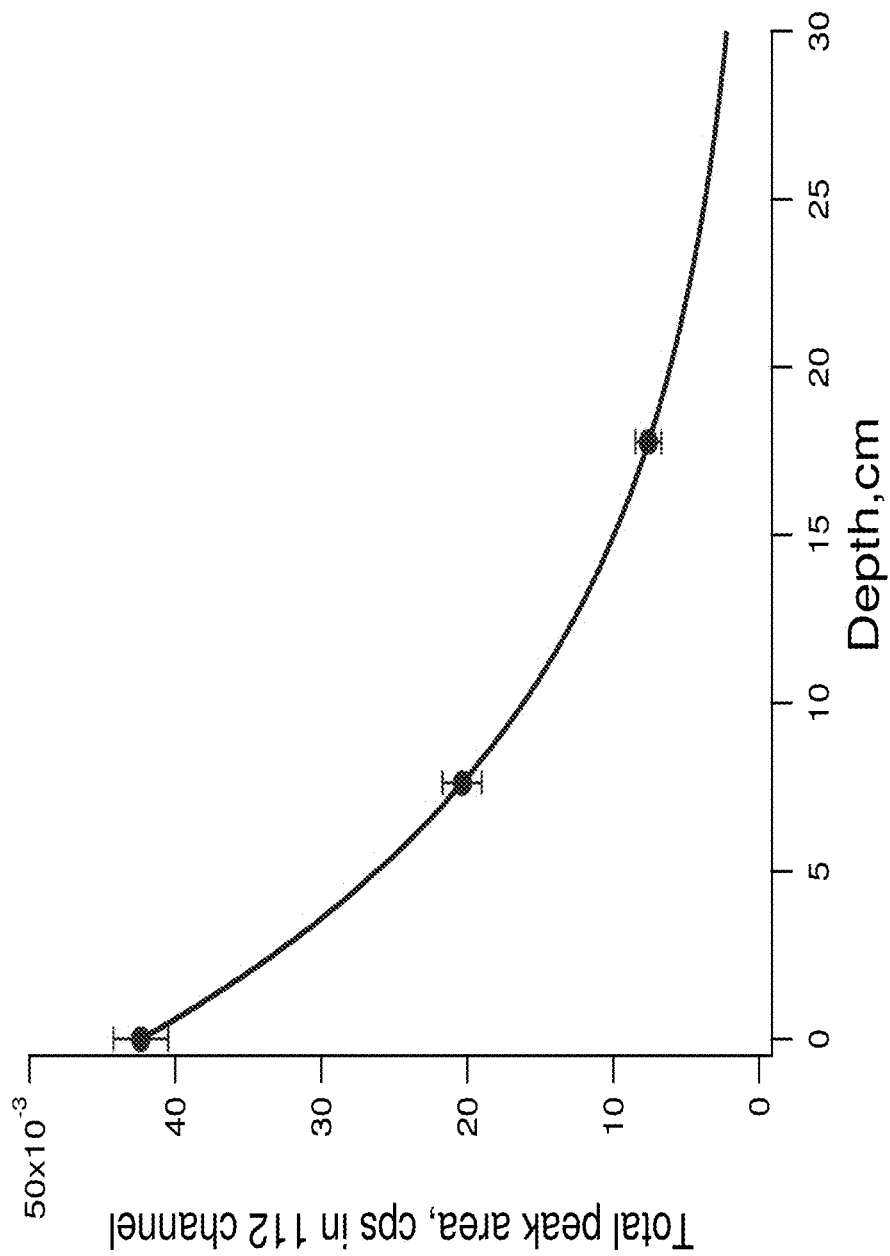
FIG. 26 shows dependence of the gamma response in "nitrogen range" versus depth from 25 kg melamine sample buried into the sand.

To calculate the nitrogen associated gamma response, the neutron stimulated gamma spectra of sand was subtracted from the melamine spectra. The resulting spectra in the "nitrogen range" was approximated by three Gaussian peaks and a total area of these three peaks was calculated. The dependence of the "nitrogen" response versus soil depth is represented in FIG. 26. As can be seen, the signal from a soil depth down to 20 cm in dry sand was quite sufficient for the detection of a 25 kg nitrogen containing object (67 N w %).

The Nitrogen Response Measurement by the INS System without Moderator

The current modification of the "MINS system" equipment at the National Soil Dynamics Laboratory does not include a moderator. On the other hand, the nitrogen containing substances of interest consist mainly of light elements (H, O, N, and C). Therefore, such substances can serve as a moderators themselves. So, measurements using the system described above without a moderator were also conducted. The measurements of neutron stimulated gamma spectra from melamine samples were conducted with and without a moderator. Results of measurements are shown in FIG. 27.

Figure 27:
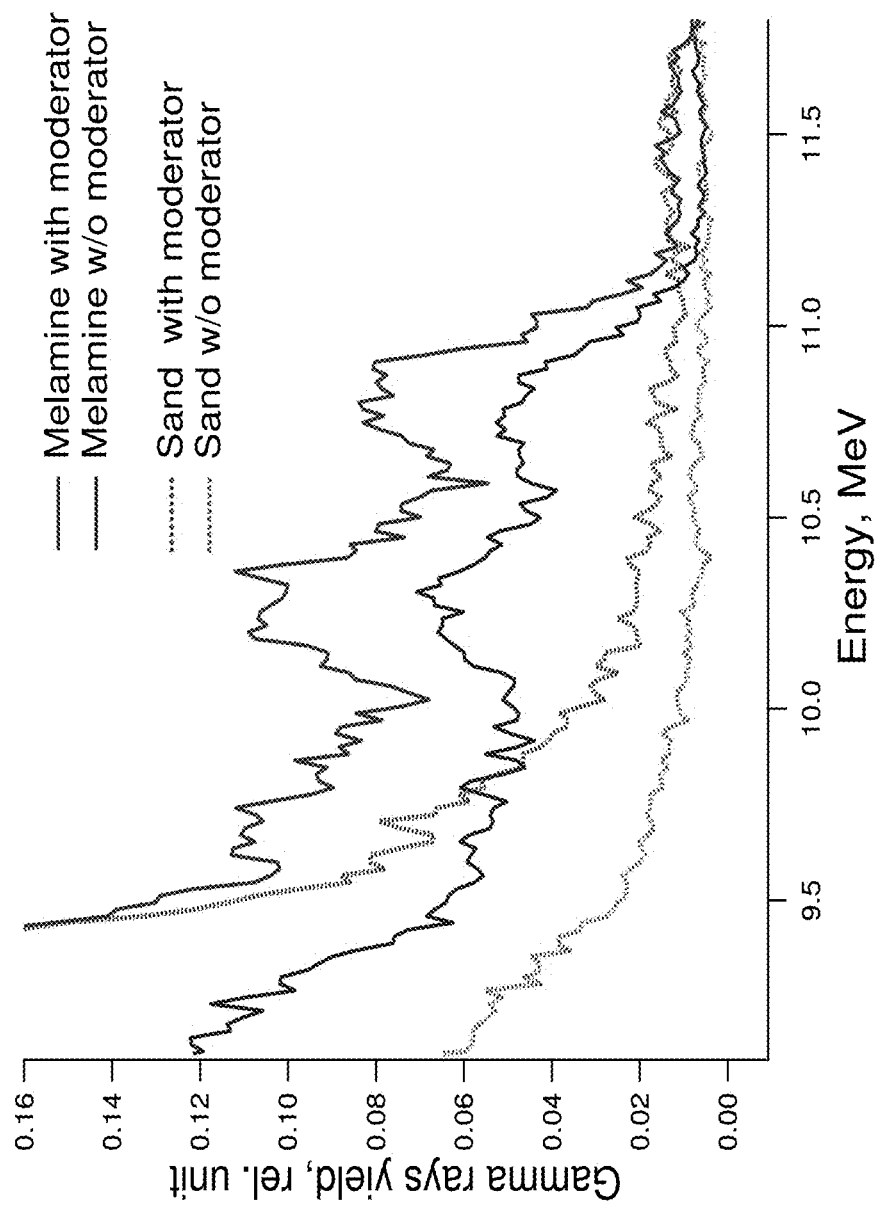
FIG. 27 shows a Comparison the TNC gamma spectra of melamine bag (25 kg) on sand pit measured with and without PE moderator (1 det, BPE+Pb shielding; R det-NG=45 cm).

As can be seen from FIG. 27, the "nitrogen" signal is smaller with the absence of the polyethylene moderator, but is still sufficient for the identification of the presence of "nitrogen" in the samples. The INS spectra at measurements without moderator, acquired simultaneously with TNC spectra, can provide information regarding the presence (and amount) of other elements, for instance, carbon. Therefore, in many cases, measurement without the moderator would be preferable by comparison with measurement with moderator.

The count rates at measurement in quasi-scanning regime can be done for the detection of buried objects containing nitrogen. An experiment was conducted using a 25 kg bag of melamine buried in the ground at a 10 cm depth. A count rate measurement was carried out using 50 channels in the range of the nitrogen peaks. One measurement took 30 second.

Figure 28:
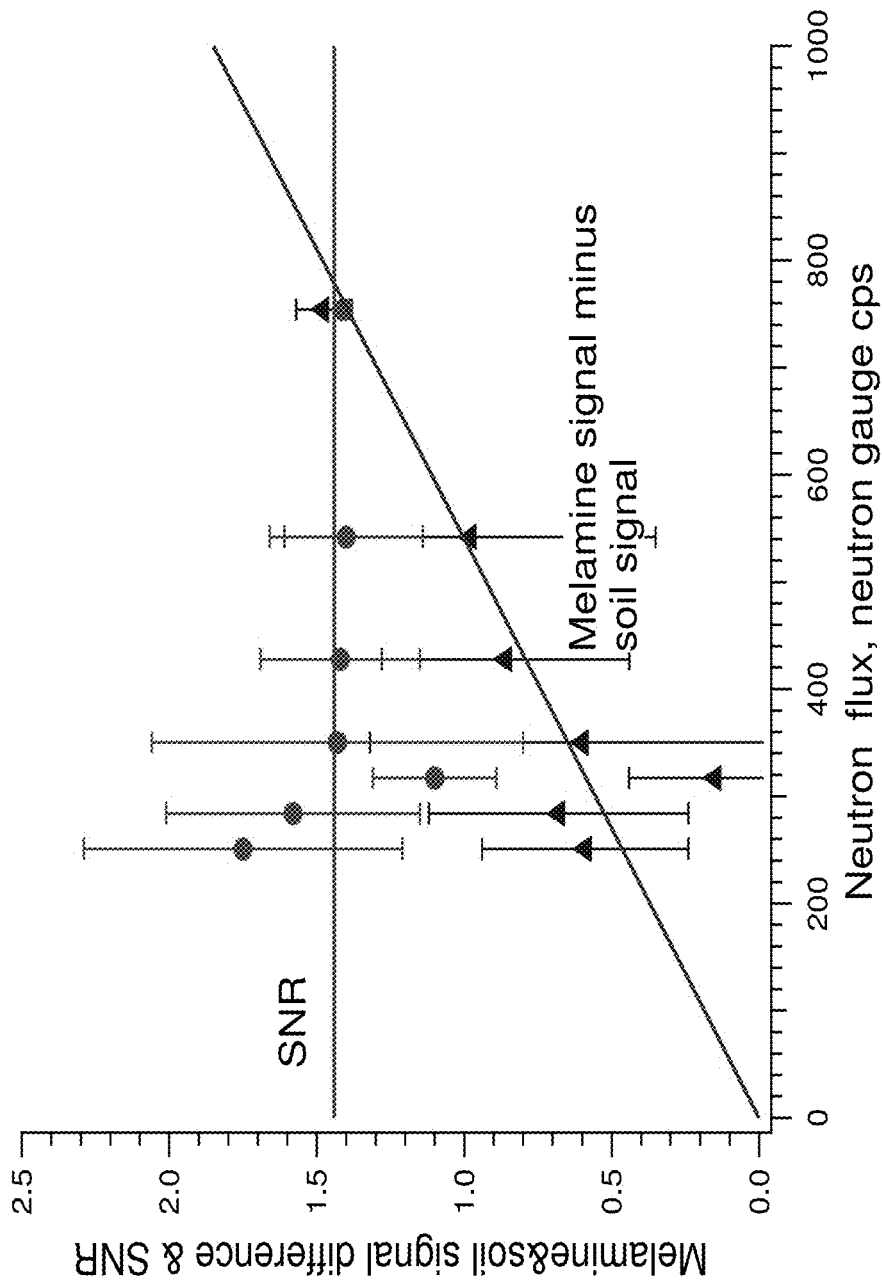
FIG. 28 shows the difference between signal and noise and SNR for TNC signal over melamine bag in soil (depth=10 cm, 510-562 ch, time of measurement=30 s; mass of sample=25 kg, 1 det, BPE+Pb shielding; distance det-NG=45 cm). Points with error bar—results of measurement; lines—approximation.

Previously, the dependencies of the system sensitivity to nitrogen, signal to noise ratio and difference between buried sample signal and background signal with intensity of neutron flux were investigated. Neutron flux was varied by changing the voltage and current of the neutron generator. Results are demonstrated in FIG. 28. As can be seen, the SNR did not change with neutron flux changes, but the signals differed with increased neutron flux. The upper limit to be used with the neutron flux (voltage and current on the neutron generator) was chosen considering the long term stability of the neutron generator and the gamma detector dead time limit (should be ≤20%). The measurements were done at: I=60 µA, V=60 kV (approximately 750 cps of neutron gauge, see FIG. 28).

Figure 29:
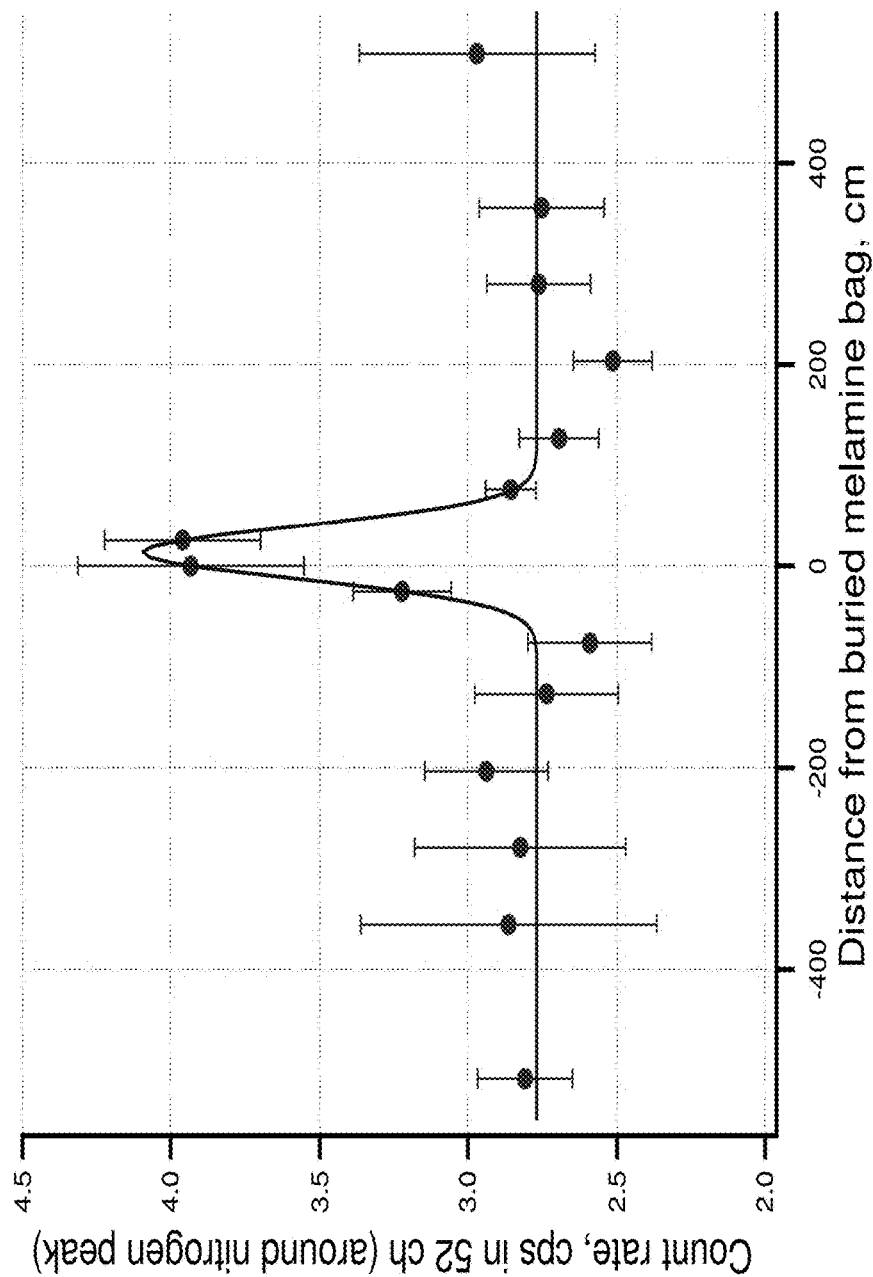
FIG. 29 shows the Signal from nitrogen vs distance from 25 kg buried on 10 cm melamine bag (time of measurement is 30 s, 5 measurement was done on each point, and average values and STD were calculated). Points with error bar—results of measurement and the line shows the Gaussian approximation.

Experiments to demonstration the possibility of using the system to detect a buried object which contains nitrogen was conducted. The measurement system (sees FIG. 18, also see FIGS. 1.A, 1.B, and FIG. 2) was moved along a path which passed over a buried object which captained nitrogen. The system was stopped every 30 cm and a 5 count rate measurements lasting 30 second each were conducted. The results of these measurement are shown in FIG. 29. Measurements conducted above the burying melamine bag increased the count rate which indicated the presence of a nitrogen containing object.

C/N Ratio Determination

The non-invasive determination of the C/N atomic or mass ratio can be used for determining the type of explosive in a material being studied. For example, the values of atomic ratio for some explosive and for tested materials are given in Table 7. The determination of the C/N atomic or mass ratio can be done with the analysis of gamma spectra measured at neutrons irradiation of an object being studied. One of the analysis technique for doing this is given in Mitra (2012). In that analysis technique, three broad regions-of-interest (ROI) between 4-7.5 MeV of a gamma spectrum are considered. The system of three equations with three unknowns, namely C, N, and O are equated and the solution is a maximum count from each of these elements, and from that the C/N and C/O ratios are found. However, this method of C/N ratio determination results in an error of approximately ±0.25.

TABLE 7

Characteristics of some explosive and tested materials

| Name of material | Chemical formula | C/N | Reference |
|---|---|---|---|
| Explosive D | mix | 1.5 | [Mitra 2012] |
| TNT | $C_7H_5N_3O_6$ | 2.33 | [Mitra 2012] |

TABLE 7-continued

Characteristics of some explosive and tested materials

| Name of material | Chemical formula | C/N | Reference |
|---|---|---|---|
| Composition B | mix | 0.95 | [Mitra, 2012] |
| Melamine | $C_3H_6N_6$ | 0.5 | — |
| Urea | $N_2H_4CO$ | 0.5 | — |

Conventional equipment for soil carbon content determination [Yakubova, 2014] consists of a neutron generator MP320, NaI(Tl) gamma-detectors with split electronics, and construction parts (shielding, mechanical chassis, power system). The adjusting parameters of the split electronic system has the possibility to expand the gamma rays registration range from 8 MeV (current) to 12 MeV. The registration of nitrogen gamma response (10.83 MeV) from studied objects can be done with TNC spectra in expanded range of gamma rays registration, while the carbon registration can be done as at soil carbon content measurement by 4.43 MeV peak in INS spectra.

Measurements of INS and TNC gamma spectra of carbon-nitrogen containing materials were undertaken using experimental setup shown in FIG. 18 without moderator. The samples and experimental setup were placed on the sand pit. The shielding from water and lead was used during these measurements. Different mixtures of ammonium nitrate and granulated coconut shell (carbon) were prepared for investigating the gamma spectra of different ratios of nitrogen-carbon containing materials. As a result of this investigation, calibration dependence of carbon/nitrogen gamma signals ratio versus C/N atomic ratio were plotted. The samples were prepared by mechanical mixing and amounts of components are shown in Table 8. The sample was placed in a stainless steel box 40×40×20 cm$^3$ and occupied ~9/10 by volume. The specific weight or volume of each sample was determined. The box with sample for measurement was placed on the surface of a sand pit under the neutron generator.

TABLE 8

Characteristics of the samples

| Sample # | Weight of ammonium nitrate, kg | Weight of coconut shells (C), kg | Atomic ratio C/N | Carbon weight percent | Density of sample, g/cm$^3$ |
|---|---|---|---|---|---|
| 1 | 22.7 | 1.419 | 0.208 | 5.9 | 0.96 |
| 2 | 22.7 | 2.838 | 0.416 | 11.1 | 0.91 |
| 3 | 22.7 | 4.431 | 0.65 | 16.3 | 0.87 |
| 4 | 22.7 | 6.135 | 0.9 | 21.3 | 0.84 |
| 5 | 22.7 | 8.18 | 1.2 | 26.5 | 0.81 |

The atomic C/N ratio, $R_{C/N}$, in sample was calculated as $$R_{C/N} = \frac{m_C}{Mw_C} \bigg/ \frac{m_{N_2H_4O_3} \cdot 2}{Mw_{N_2H_4O_3}}$$

where $m_C$, $m_{N_2H_4O_3}$ are the carbon and ammonium nitrate masses in mixture, $Mw_C$, $Mw_{N_2H_4O_3}$ are the carbon and ammonium nitrate molecular weights, 2 is the nitrogen atoms number in molecule.

Carbon weight percent Cw % in mixture was calculated by equation $$Cw\% = \frac{R_{C/N}}{Mw_{N_2H_4O_3}/2 \cdot Mw_C + R_{C/N}}$$

Density of sample $d_{mix}$ was calculated as $$d_{mix} = \frac{d_{N_2H_4O_3} \cdot d_C}{d_C \cdot Cw\% + d_C \cdot (1 - Cw\%)}$$

where $d_{N_2H_4O_3}=1.009$ g/cm$^3$, $d_C=0.52$ g/cm$^3$ are the densities of ammonium nitrate and carbon.

Figure 30:
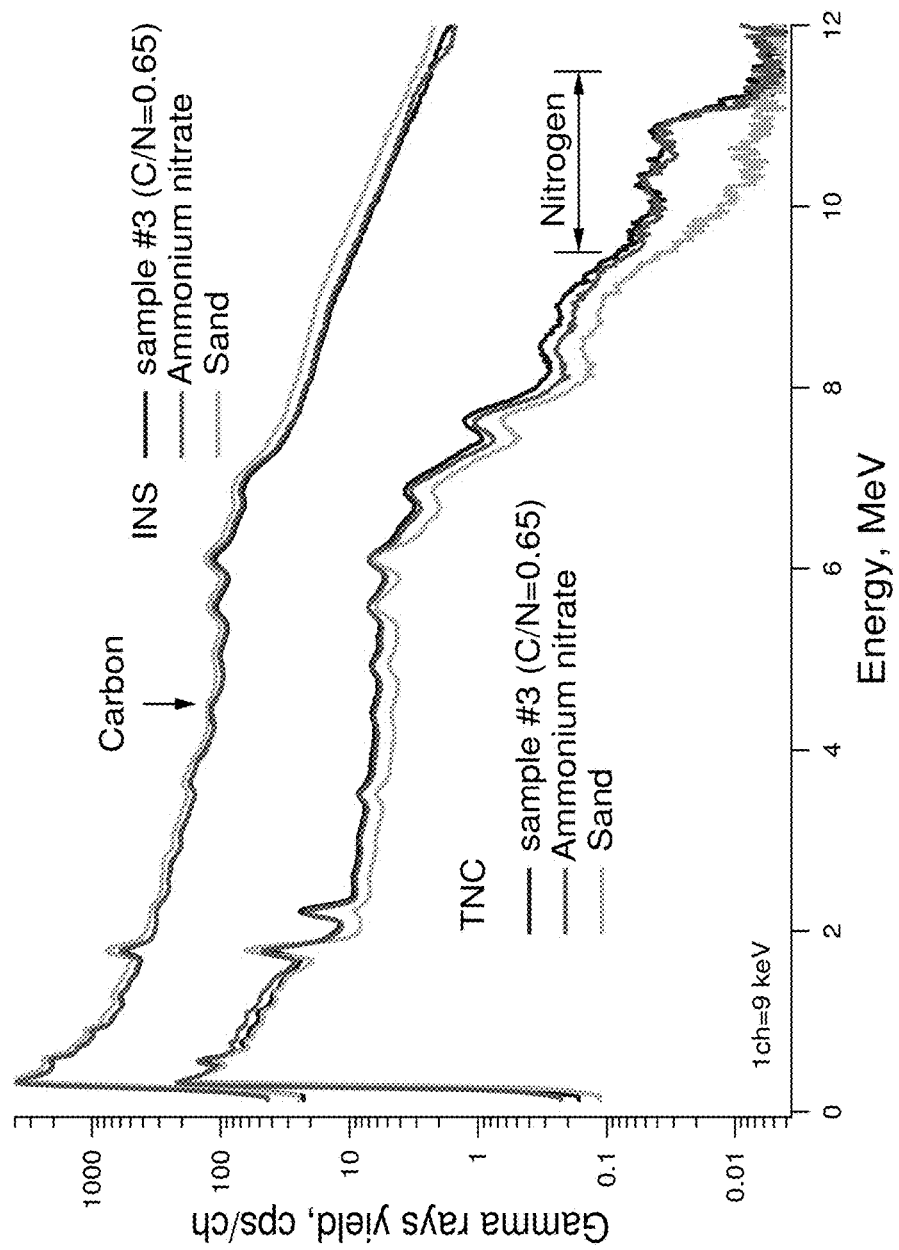
FIG. 30 shows experimental gamma spectra data.

Examples of INS and TNC spectra of one the sample (#3 ammonium nitrate and sand) are demonstrated in FIG. 30.

Figure 31:
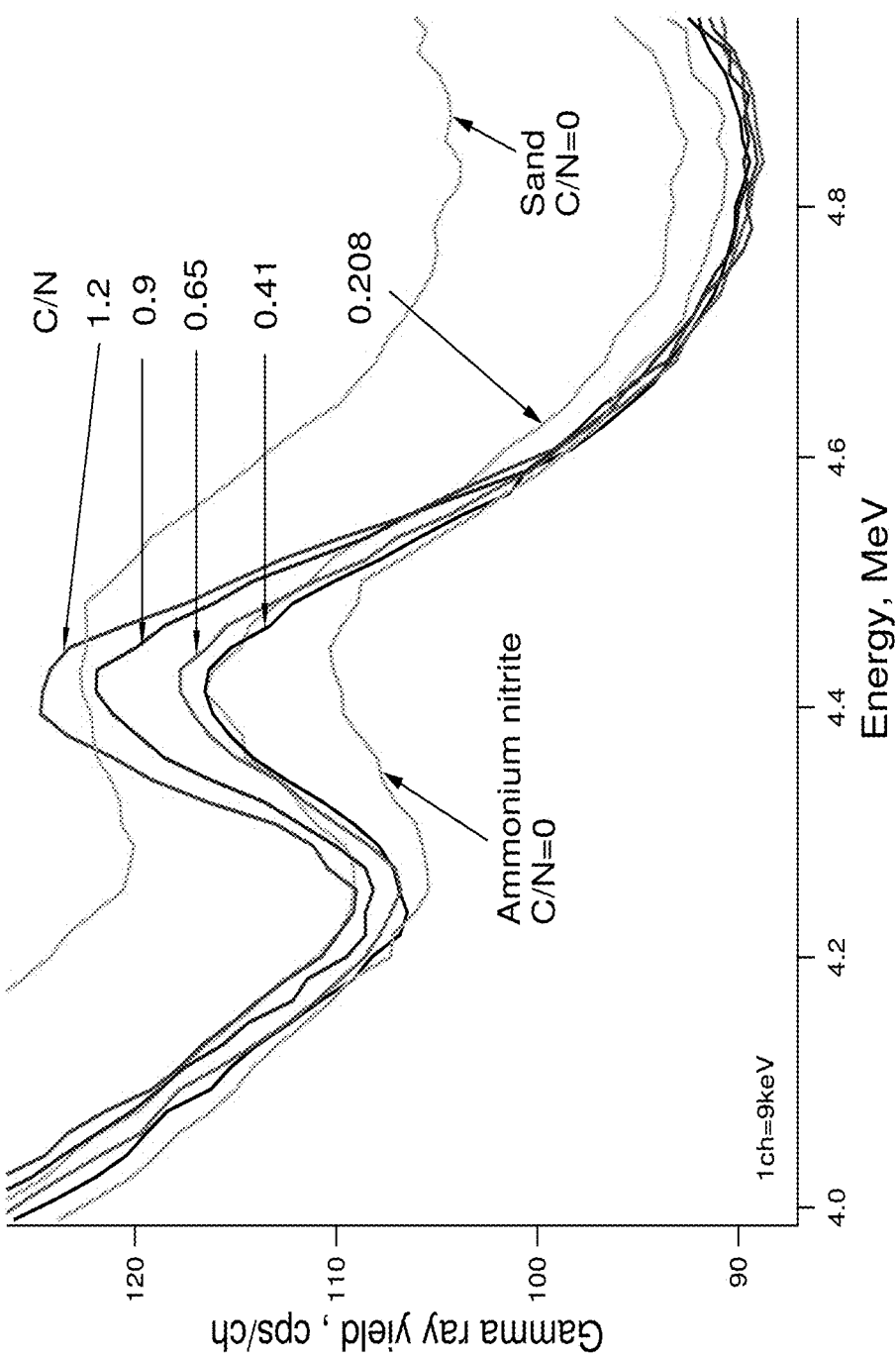
FIG. 31 shows net carbon peak for different C/N ratios.
Figure 32:
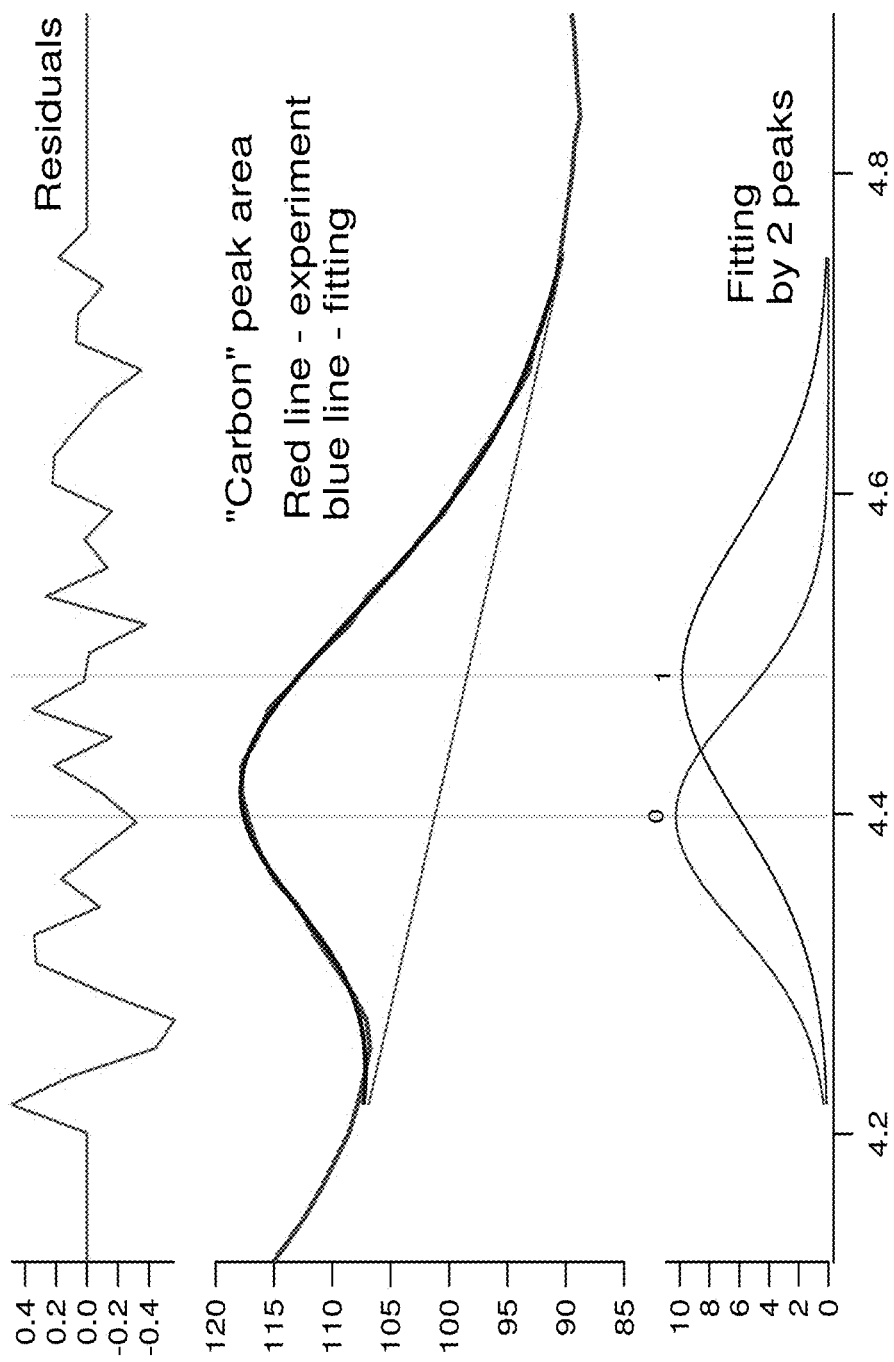
FIG. 32 shows fitting "carbon" peak area for a m Mixture of ammonia nitrate and 16.3 w % of coconut shells (C) on a sand pit. C/N=0.65.
Figure 33:
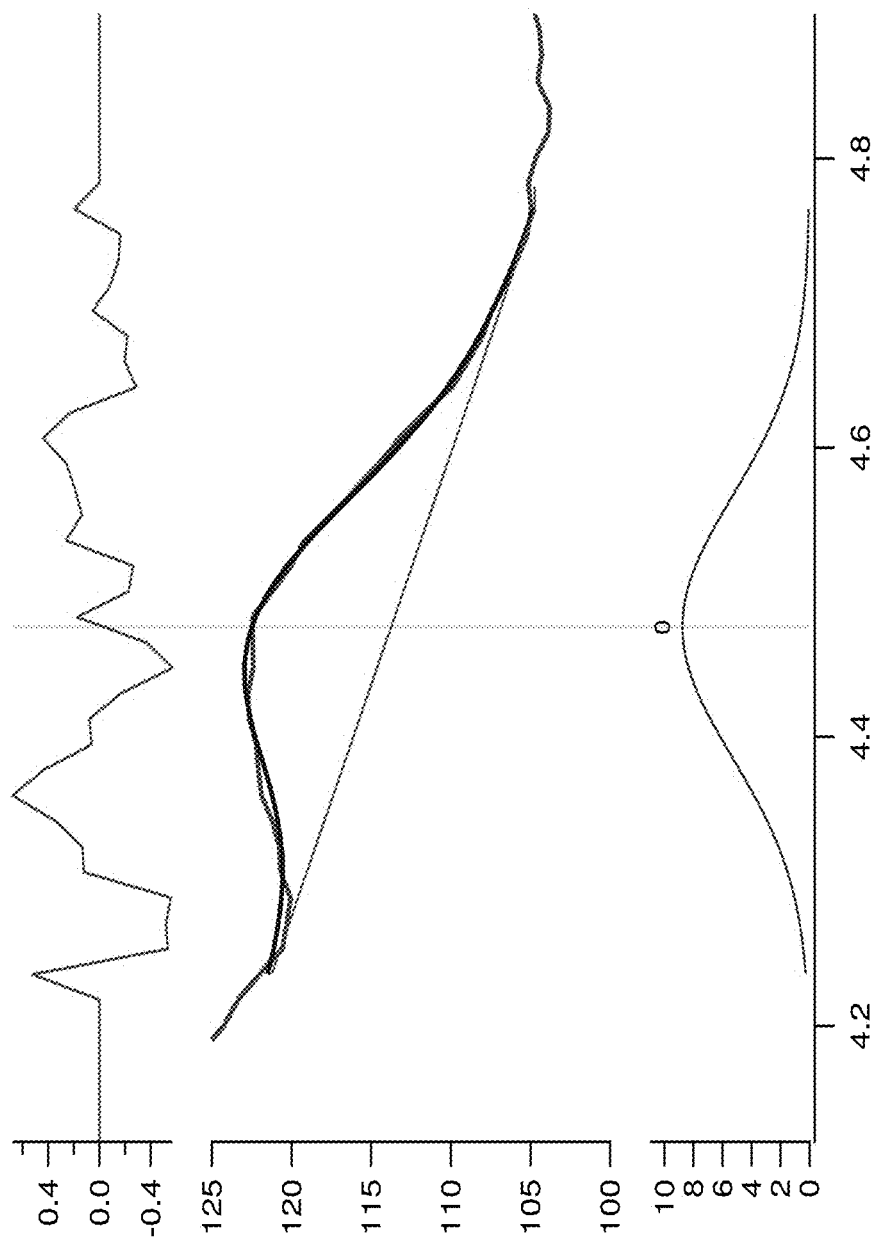
FIG. 33 shows fitting "carbon" peak area for sand.
Figure 34:
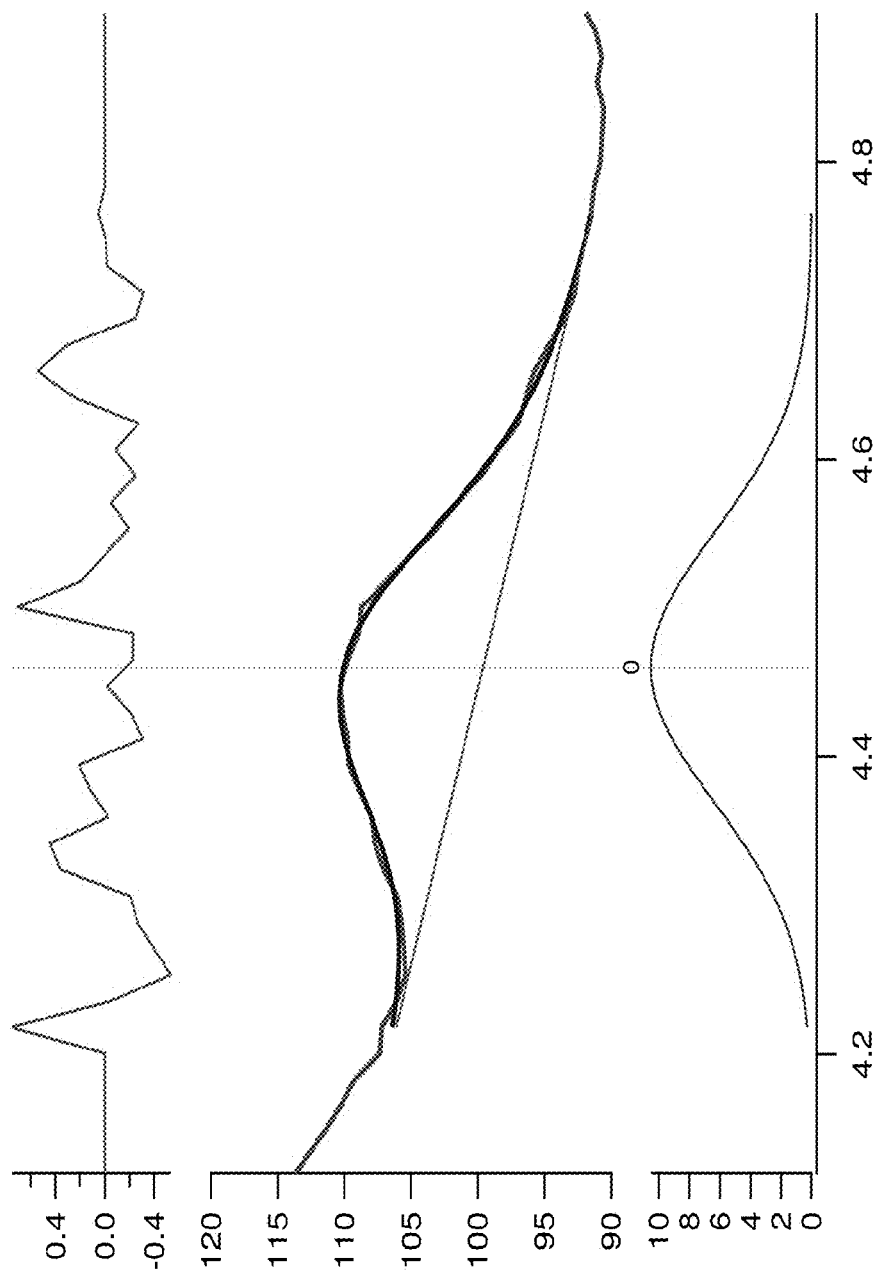
FIG. 34 shows fitting "carbon" peak area for Ammonium nitrate on sand pit.

The carbon and nitrogen peaks are denoted in the figure. To extract the net carbon peak area in this research, the net-INS spectra [Yakubova, 2015] were determined by subtraction of TNC spectra from INS spectra channel by channel (FIG. 30). Then the area in net-INS spectra around the carbon peak was fitted by one or two Gaussian peaks. As can be seen from FIGS. 31 and 32, the "carbon" peak of both sand and ammonium nitrate can be fitted by one peak with centroid near 4.5 MeV. This peak can be associated with cascade transition in silicon-28 due to inelastic neutron scattering [Wielopolski, 2011; Mitra, 2012; Kavetskiy, 2014]. The possible appearing of the peak with centroid 4.4 MeV, carbon-12, due to O-16(n,nα)C-12 and N-14(n,t)C-12 nuclear reactions (threshold energy>12 MeV) was not observed in the conditions of our measurement. Because the 14 MeV neutron energy drops below that threshold energy for the first 1-2 collision with sample nuclei, the effect of these reactions are most likely negligible. However, with the addition of coconut shells (carbon) into the mixture a second component with centroid around 4.4 MeV in net-INS spectra in "carbon" peak appears. In gamma spectra of ammonium nitrate and carbon mixtures, the "carbon" can be fitted by two peaks: with centroid at 4.5 MeV (is attributed to Si-28 in sand) and with centroid at 4.4 MeV. This peak can be directly attributed to carbon in mixture. The area of this peak is proportional to the amount of carbon in the sample.

Figure 35:
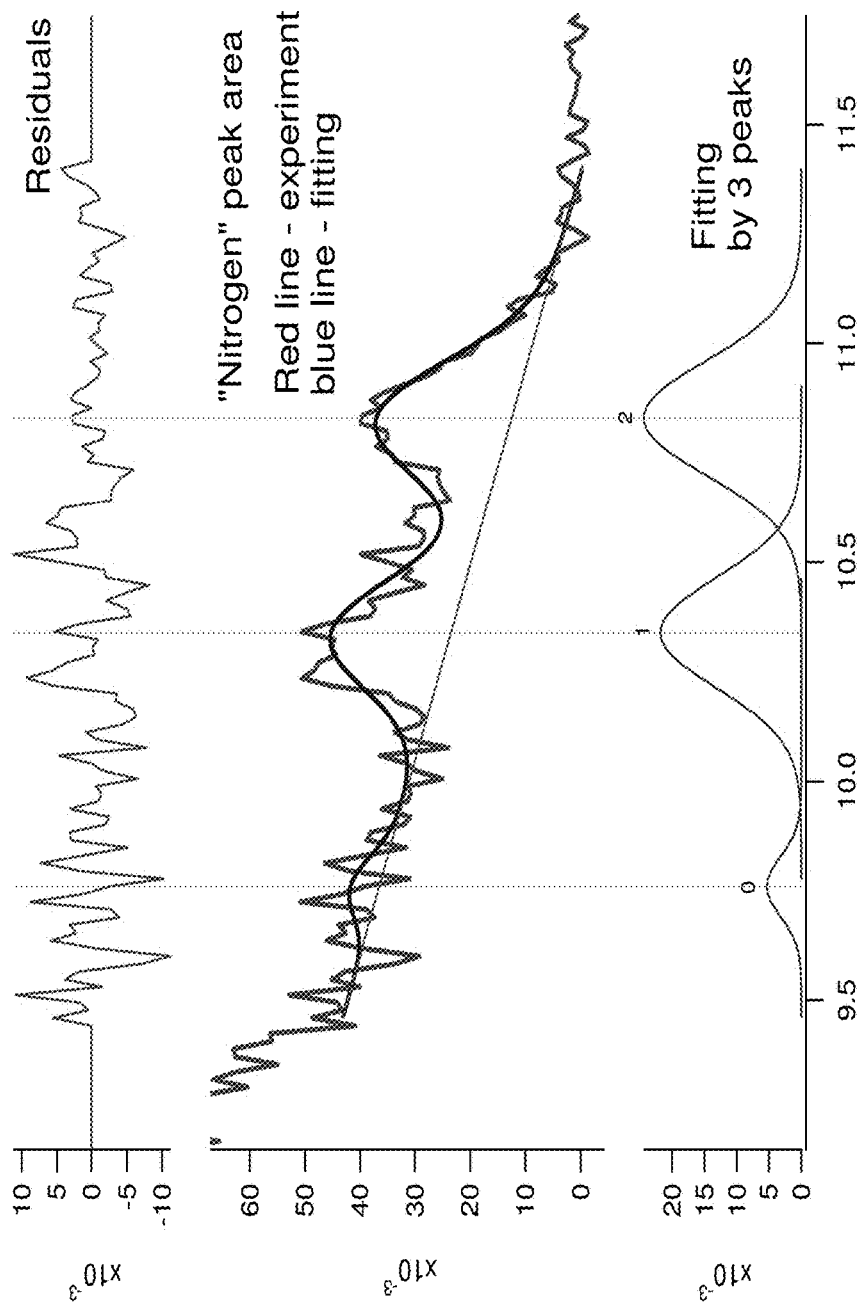
FIG. 35 shows fitting "nitrogen" peak area.

Three peaks in "nitrogen" peak area in TNC spectra are directly connected with nitrogen in sample as was mentioned above. Again, the difference between TNC sample spectrum and TNC sand spectrum was calculated in channel by channel. This area was fitted by three Gaussian peaks with centroid around 10.8 MeV, 10.3 MeV, and 9.8 MeV as shown in FIG. 35. The total peaks area was associated with nitrogen in sample.

Figure 36:
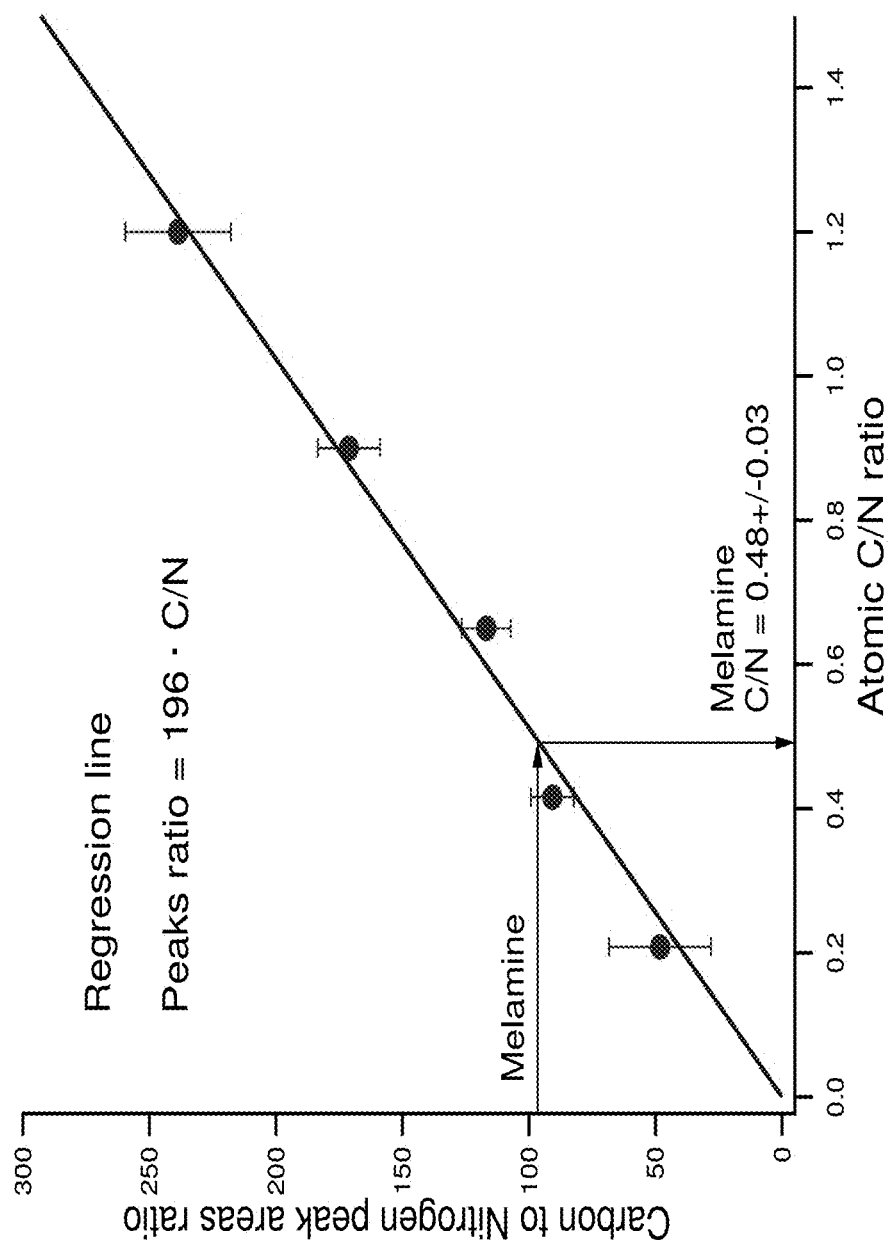
FIG. 36 shows "carbon" to "nitrogen" peak areas ratio versus atomic C/N ratio.

The peak areas connected with carbon (in net-INS spectra) and sum of three peak areas connected with nitrogen (in TNC spectra) are summarized in Table 9. The "carbon" to 'nitrogen" peak areas ratio was plotted versus atomic C/N ratio in samples in FIG. 36. The regression line of the two ratios was calculated, and, as can be seen, the dependence of carbon to nitrogen peak areas ratio versus C/N atomic ratio is directly proportional.

The measurements of neutron stimulated gamma spectra of a bag with melamine (25 kg) was also done. The result of determination of "carbon" to "nitrogen" peak areas and their ratio are also presented in Table 9. Using regression line equation, the value of C/N atomic ratio for melamine can be determined. The value calculated was 0.48±0.03, which is in the frame of the experimental error for the carbon to nitrogen ratio of melamine.

TABLE 9

Sample (and Melamine) evaluation

| Sample # | C/N atomic ratio | Peaks area in "carbon" range with centroid at ± error, cps | | Sum of peak areas in "nitrogen" range ± error, cps | Ratio of "carbon" peak area to "nitrogen" peak area ± error |
|---|---|---|---|---|---|
| | | 4.4 MeV ("carbon" peak area) | 4.5 MeV | | |
| 1 | 0.208 | 0.77 ± 0.32 | 2.09 ± 0.36 | 0.0161 ± 0.0010 | 48.2 ± 20.2 |
| 2 | 0.416 | 1.57 ± 0.12 | 1.97 ± 0.06 | 0.0173 ± 0.0009 | 90.8 ± 8.4 |
| 3 | 0.65 | 1.76 ± 0.07 | 2.03 ± 0.07 | 0.0151 ± 0.0011 | 116.9 ± 9.7 |
| 4 | 0.90 | 2.77 ± 0.07 | 1.85 ± 0.07 | 0.0162 ± 0.0011 | 171.2 ± 12.3 |
| 5 | 1.20 | 2.88 ± 0.07 | 2.70 ± 0.07 | 0.0121 ± 0.0010 | 238.7 ± 20.7 |
| Melamine | 0.50 | 2.88 ± 0.12 | — | 0.0304 ± 0.0002 | 94.6 ± 6.0 |

For the foregoing reasons, it is clear that the method and apparatus described herein provides an innovative carbon and/or nitrogen detection system that may be used in multiple different applications. The current system may be modified in multiple ways and applied in various technological applications. The disclosed method and apparatus may be modified and customized as required by a specific operation or application, and the individual components may be modified and defined, as required, to achieve the desired result.

Although the materials of construction are not described, they may include a variety of compositions consistent with the function described herein. Such variations are not to be regarded as a departure from the spirit and scope of this disclosure, and all such modifications as would be obvious to one skilled in the art are intended to be included within the scope of the following claims.

The amounts, percentages and ranges disclosed herein are not meant to be limiting, and increments between the recited amounts, percentages and ranges are specifically envisioned as part of the invention. All ranges and parameters disclosed herein are understood to encompass any and all sub-ranges subsumed therein, and every number between the endpoints. For example, a stated range of "1 to 10" should be considered to include any and all sub-ranges between (and inclusive of) the minimum value of 1 and the maximum value of 10 including all integer values and decimal values; that is, all sub-ranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. As used herein, the term "about" refers to a quantity, level, value, or amount that varies by as much 10% to a reference quantity, level, value, or amount.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein). The invention illustratively disclosed herein suitably may be practiced in the absence of any element which is not specifically disclosed herein.

While the invention has been described with reference to details of the illustrated embodiments, these details are not intended to limit the scope of the invention as defined in the appended claims.

The embodiment of the invention in which exclusive property or privilege is claimed is defined as follows:

1. A detection system for determining the presence of chlorine on, or below, a testable surface, comprising:
   a neutron generator assembly, for generating pulsed neutron beams;
   a moderator, positioned between the neutron generator assembly and the testable surface;
   a gamma ray detector, positioned to detect a gamma ray response from materials on or below the testable surface when the neutron beams impinge the materials; and
   a gamma ray detector processor/controller comprising a split electronics processing system that separates gamma spectra acquired during a neutron pulse from the gamma spectra acquired between neutron pulses, the gamma ray detector processor/controller being in communication with the gamma ray detector and the neutron generator assembly, the gamma ray detector processor/controller is being structured to collect thermal neutron capture (TNC) gamma spectra data between neutron beam pulses;
   wherein, the gamma ray detector processor/controller is structured so that the presence of chlorine is indicated when the TNC gamma ray spectra data indicates a count rate peak with a centroid at about 1164 keV.

2. The detection system of claim 1 wherein neutron generator assembly comprises an accelerator tube and a neutron generator controller.

3. The detection system of claim 1 wherein the neutron generator assembly is a deuterium-tritium (D-T) generator.

4. The detection system of claim 1 wherein the neutron generator assembly generates a neutron beam with energy of 14.1 MeV.

5. The detection system of claim 1, wherein the moderator comprises polyethylene substrate.

6. The detection system of claim 5 wherein the moderator substrate is between four and six centimeters thick.

7. The detection system of claim 1 wherein the gamma ray detector is comprised of sodium iodate.

8. The detection system of claim 7 wherein the gamma ray detector has a volume of at least 2.4 $dm^3$.

9. The detection system of claim 1 wherein gamma ray shielding is positioned between the neutron generator and the gamma ray detector.

10. The detection system of claim 9 wherein the shielding comprises lead (Pb).

11. The detection system of claim 1 further comprising a monitoring/controlling computer system that is in electronic communication with the neutron generator assembly and the gamma ray detector processor/controller.

12. The detection system of claim 1 wherein the monitoring/controlling computer system comprises a computer laptop.

13. The detection system of claim 12 wherein the laptop is used to control the detection system.

14. The detection system of claim 1 wherein the detection system is portable.

15. The detection system of claim 1 wherein the testable surface is soil.

16. A method of determining the presence or absence of chlorine on, or below, a testable surface; the method comprising the steps of:
   (a) providing the detection system as described in claim 1;
   (b) moving the detection system to a position above the testable surface;
   (c) generating a pulsed neutron beam with the neutron generator assembly;
   (d) detecting gamma ray spectra data with the gamma ray detector;
   (e) collecting and processing the gamma ray spectra data with the gamma ray detector processor/controller;
   (f) determining whether the TNC gamma ray spectra data indicates a count rate peak with a centroid at about 1164 keV and therefore chlorine is present; otherwise, chlorine is not present.

17. The method of claim 16 wherein, in step (a) a monitoring/controlling computer system comprising a laptop computer is also provided, the laptop computer monitor visually indicating a presence of chlorine.

18. The method of claim 16 wherein, in step (c), the gamma ray detector comprises an NaI(Tl).

19. The method of claim 16 wherein, in step (e), the gamma ray detector processor/controller collects and processes TNC data between neutron beam pulses.

* * * * *